US012612374B2

(12) United States Patent
Lubec

(10) Patent No.: US 12,612,374 B2
(45) Date of Patent: Apr. 28, 2026

(54) THIAZOLE AND DIPHENYL SUBSTITUTED SULFOXIDES FOR USE IN IMPROVING COGNITION FUNCTIONS AND AGAINST ADDICTIONS TO SUBSTANCES

(71) Applicant: Cogmotiv FlexCo, Vienna (AT)

(72) Inventor: Gert Lubec, Vienna (AT)

(73) Assignee: Cogmotiv FlexCo, Vienna (AT)

( * ) Notice: Subject to any disclaimer, the term of this patent is extended or adjusted under 35 U.S.C. 154(b) by 938 days.

(21) Appl. No.: 17/642,685

(22) PCT Filed: Sep. 10, 2020

(86) PCT No.: PCT/EP2020/075338

§ 371 (c)(1),
(2) Date: Mar. 12, 2022

(87) PCT Pub. No.: WO2021/048284

PCT Pub. Date: Mar. 18, 2021

(65) Prior Publication Data

US 2022/0324821 A1 Oct. 13, 2022

(30) Foreign Application Priority Data

Sep. 13, 2019 (EP) .................................... 19197359

(51) Int. Cl.
*C07D 277/26* (2006.01)
*A61P 25/28* (2006.01)

(52) U.S. Cl.
CPC ............ *C07D 277/26* (2013.01); *A61P 25/28* (2018.01)

(58) Field of Classification Search
CPC .................................................... C07D 277/26
See application file for complete search history.

(56) References Cited

U.S. PATENT DOCUMENTS

| | | | |
|---|---|---|---|
| 2002/0183334 | A1 | 12/2002 | Bacon et al. |
| 2005/0234040 | A1 | 10/2005 | Bacon et al. |

FOREIGN PATENT DOCUMENTS

| | | | |
|---|---|---|---|
| CN | 107522693 | B | 12/2018 |
| EP | 2 292 213 | A1 | 3/2011 |
| WO | 03/059873 | A1 | 7/2003 |
| WO | 03/066035 | A2 | 8/2003 |
| WO | 2016/023997 | A1 | 2/2016 |

OTHER PUBLICATIONS

Heidi Moawad, What is Cocaine Addiction? How to Spot the Signs and Find Treatment; Jun. 22, 2022; URL: https://www.verywellhealth.com/cocaine-addiction-5088370?*

Alzheimer's disease [online] retrieved from the internet on Mar. 25, 2022 URLhttps:/www.mayoclinic.org/diseases-conditions/alzheimers-disease/symptoms-causes/syc-.*

Chen,et al. Amyloid beta:structure, biology and structure-based therapeutic development. ActaPharmacologicaSinica2017:1205-1235.*

International Search Report and Written Opinion, mailed Feb. 12, 2020, for International Application No. PCT/EP2020/075338. (9 pages).

* cited by examiner

*Primary Examiner* — Shawquia Jackson
(74) *Attorney, Agent, or Firm* — Seed Intellectual Property

(57) ABSTRACT

The present disclosure relates to a chemical compound having the general formula (I):

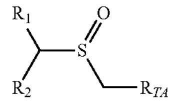

wherein $R_1$ is a phenyl group and $R_2$ is a meta-substituted phenyl group; and $R_{TA}$ is a substituted or unsubstituted thiazole ring. The disclosure also relates to said compound according to formula (I), in particular in its diastereomerically pure or enriched form, for use in therapy, in particular for treating and/or preventing age-related cognitive decline. Further, the disclosure relates to said compound according to formula (I) for use in improving cognitive functions, in particular for use in improving the spatial learning capabilities in human individuals. And, disclosure also relates to said compound according to formula (I) for use in the treatment and/or prevention of alcohol addiction, nicotine addiction and/or drug addiction, in particular cocaine and/or metamphetamine addiction.

13 Claims, 3 Drawing Sheets

Fig. 1: Synthesis of compounds 1_1, 1_2, 2_1, 2_2

1, 2, 3, 4, 6

7, mix_1, 5

8, mix_2

5-(((S)-((S)-(3-bromophenyl)(phenyl)methyl)sulfinyl)methyl)thiazole

**1_1 $S_1$ (*S*) $C_1$ (*S*)**

5-(((R)-((S)-(3-bromophenyl)(phenyl)methyl)sulfinyl)methyl)thiazole

**1_2 $S_1$ (*R*) $C_1$ (*S*)**

5-(((S)-((R)-(3-bromophenyl)(phenyl)methyl)sulfinyl)methyl)thiazole

**2_1 $S_1$ (*S*) $C_1$ (*R*)**

5-(((R)-((R)-(3-bromophenyl)(phenyl)methyl)sulfinyl)methyl)thiazole

**2_2 $S_1$ (*R*) $C_1$ (*R*)**

THIAZOLE AND DIPHENYL SUBSTITUTED SULFOXIDES FOR USE IN IMPROVING COGNITION FUNCTIONS AND AGAINST ADDICTIONS TO SUBSTANCES

BACKGROUND

Technical Field

The present disclosure relates to diastereomeric compounds that can be used to improve cognitive functions, in particular learning capabilities and memory performance, more in particular to improve spatial memory, in human individuals, in particular in aging individuals. More in particular, the present disclosure refers to new compounds which can be used to treat age-dependent decline of cognitive functions such as spatial memory tasks.

Description of the Related Art

Cognitive decline during aging represents a serious medical and socioeconomic burden in societies with high life expectancy. Aging-induced cognitive impairment is often paralleled by a decrease of dopamine in various brain regions. Dopamine plays a fundamental role in learning and memory involving intrinsic neuronal circuits in the prefrontal cortex and the hippocampus as well as the neuronal network activity between these structures (Werlen et al., Modulating the map: dopaminergic tuning of hippocampal spatial coding and interactions, Prog. Brain Res. 219:187-216; 2015). The effects of dopamine as a target of treating cognitive disorders, however, depend on the memory systems engaged (Ashby et al., Differential effects of dopamine-directed treatments on cognition, Neuropsychiatr. Dis. Treat. 11:1859-1875; 2015). Spatial memories that structurally involve the hippocampus and prefrontal-cortex and declarative (Linssen et al., Methylphenidate produces selective enhancement of declarative memory consolidation in healthy volunteers, Psychopharmacology (Berl), 221:611-619; 2012) and novelty (Takeuchi et al., The synaptic plasticity and memory hypothesis: encoding, storage and persistence, Philos. Trans. R Soc Lond B Biol Sci. 369: 20130288; 2013) memory processes strongly depend on neuromodulatory functions of dopamine. Further, the connectivity between these brain structures (Bertolino et al., Prefrontal-hippocampal coupling during memory processing is modulated by COMT val158met genotype. Biol. Psychiatry. 60:1250-1258; 2006) as well as synaptic glutamatergic transmission within these structures is strongly influenced by dopamine mainly by the release from the ventral tegmental area. Basal ganglia can be involved in the modulation of non-declarative memories (Foerde and Shohamy, The role of the basal ganglia in learning and memory: insight from Parkinson's disease, Neurobiol. Learn. Mem. 96:624-636; 2011), such as the nucleus accumbens (Mulder et al., Short- and long-term plasticity of the hippocampus to nucleus accumbens and prefrontal cortex pathways in the rat, in vivo, Eur. J. Neurosci 9:1603-1611; 1997; López et al., Opposite effects of shell or core stimulation of the nucleus accumbens on long-term potentiation in dentate gyrus of anesthetized rats, Neuroscience 151:572-8; 2008) and striatum (Sagratella et al., Selective reduction of hippocampal dentate frequency-potentiation in striatally lesioned rats with impaired place learning, Brain Res. 660: 66-72; 1994, in conjunction with declarative memory).

The inhibition of the dopamine transporter (DAT) has been targeted to circumvent the problems of task and age dependent functional differences of the dopaminergic system. DAT reuptakes extracellular dopamine into the synapse. Accordingly, the application of dopamine transporter inhibitors (DAT-inhibitors) leads to an increase of extracellular dopamine concentrations (Rowley et al., Differences in the neurochemical and behavioural profiles of lisdexamfetamine methylphenidate and modafinil revealed by simultaneous dual-probe microdialysis and locomotor activity measurements in freely-moving rats, J. Psychopharmacol. 28:254-69; 2014), from which a variety of dopamine receptors can benefit.

Cognitive functions can be influenced and improved by a series of chemical compounds including medication targeting the dopamine transporter (DAT). The dopamine transporter reuptakes extracellular dopamine into the synapse, and inhibitors increase the extracellular concentration of dopamine (Rowley et al., 2014), which then can lead to an improvement of learning and memory. For example, it has been shown that DAT inhibitors affect hippocampal synaptic plasticity in the dentate gyrus (Tsanov et al., The psychostimulant modafinil facilitates water maze performance and augments synaptic potentiation in dentate gyrus, Neuropharmacology 59:9-19; 2010; Jenson et al., Dopamine and norepinephrine receptors participate in methylphenidate enhancement of in vivo hippocampal synaptic plasticity, Neuropharmacology 90:23-32; 2015) and CA1 (Swant and Wagner, Dopamine transporter blockade increases LTP in the CA1 region of the rat hippocampus via activation of the D3 dopamine receptor, Learn Mem. 13:161-167; 2006) as well as working memory and long-term memory in different learning tasks (including spatial tasks) in rodents (Burgos et al., Effect of modafinil on learning performance and neocortical long-term potentiation in rats, Brain Res. Bull. 83:238-44; 2010; Li et al., Balanced dopamine is critical for pattern completion during associative memory recall, PLoS One. 5(10) e15401. doi: 10.1371/journal.pone.0015401, 2010; Tsanov et al., The psychostimulant modafinil facilitates water maze performance and augments synaptic potentiation in dentate gyrus. Neuropharmacology. 59:9-19, 2010) and humans (Zilles et al., Genetic polymorphisms of 5-HTT and DAT but not COMT differentially affect verbal and visuospatial working memory functioning, Eur Arch Psychiatry Clin Neurosci., 2012 December; 262(8):667-76). Commonly used inhibitors, however, exert insufficient specificity for DAT and inhibit also noradrenaline and serotonin transporters. This unspecificity can lead to severe side effects on the general arousal level and induces psychiatric like disorders such as depressive attacks (Wood et al., Psychostimulants and cognition: a continuum of behavioral and cognitive activation, Pharmacol. Rev. 66:193-221; 2014).

Aging related decline in cognitive abilities goes along with degenerated dopaminergic systems in various brain regions including hippocampus and prefrontal cortex. Pre- and post-synaptic dopaminergic components are thereby differently changed across the life-span thereby impairing cognitive functions such as working and episodic memory and decision making differently (Li and Rieckman, Neuromodulation and aging: implications of aging neuronal gain control on cognition, Curr. Opin. Neurobiol. 29:148-158; 2014) in various age classes. Further, differences in task performance may also be related to mere differences in motivation, rather than cognition.

Hippocampal glutamatergic activity as a critical mechanism of learning and memory formation is regulated by the dendritic spine, actin binding potein drebrin (Merriam et al., Synaptic regulation of microtubule dynamics in dendritic spines by calcium, F-actin, and drebrin, J. Neurosci., October 16; 33 (42):16471-82; 2013). Hippocampal dopamine-glutamate interactions are realized by a number of postsynaptic proteins like homer (de Bartolomeis and Tomasetti, Calcium-dependent networks in dopamine-glutamate interaction: the role of postsynaptic scaffolding proteins, Mol. Neurobiol., October:46(2):275-96; 2012) and presynaptic regulators of transmitter release like bassoon (Gundelfinger et al., Role of Bassoon and Piccolo in Assembly and Molecular Organization of the Active Zone. Front Synaptic Neurosci., January 12; 7:19. doi: 10.3389/fnsyn.2015.00019; 2016). cAMP as a second messenger of dopamine activated adenylate cyclases mediate dopamine downstream signaling involving protein kinase A (PKA) and the cAMP response element-binding protein (CREB) that play pivotal roles in long-term memory formation. Moreover, functional changes of dopamine via hetero-receptor complexes have been reported in the context of cognition and psychiatric diseases (Fuxe et al., Understanding the role of heteroreceptor complexes in the central nervous system, Curr Protein Pept. Sci. 2014; 15(7):647; Fuxe et al., Dopamine heteroreceptor complexes as therapeutic targets in Parkinson's disease, Expert Opin. Ther. Targets. 19:377-98; 2015; Martinez-Pinilla, Dopamine D2 and angiotensin II type 1 receptors form functional heteromers in rat striatum, Biochem. Pharmacol. 96:131-42; 2015).

The term "working memory" can be considered to be a specific form of short-term memory that refers to the ability to retain information within a single trial, i.e., to actively hold multiple pieces of transitory information in the mind where they can be manipulated in a way that makes them useful for goal directed behavior. According to Alan Baddeley (Working memory, reading and dyslexia. Advances in Psychology 34:141-152, 1986.) working memory can be defined as "a system for the temporary holding and manipulation of information during the performance of a range of cognitive tasks such as comprehension, learning, and reasoning." The long-term storage of information that remains constant over time and that is gradually acquired over many training sessions is usually assigned to the "reference memory" (D. S. Olton, Mazes, maps, and memory, American Psychologist 34:583, 1979). That is, in contrast to working memory, reference memory appears to be more comparable to long-term memory because it refers to the ability to store information about a specific fixed situation. According to Fauci et al. (in "Harrison's Principles of Internal Medicine," volume 1, pp. 142 to 150, 1988) reference memory refers to information gained from previous experience, either recent or remote, i.e., reference memory refers to knowledge for a certain situation that remains constant over time. As stated by A. N. Guitar in "The Interaction Between Spatial Working and Reference Memory in Rats on a Radial Maze" (Paper 4, 2014; http://ir.lib.uwo.ca/psychd_uht) working memory and reference memory could be defined as independent systems both cognitively and physically. Accordingly, reference memory is or can be compared to long-term memory. The reference memory usually is gradually acquired over many training sessions. Once stored, the reference memory is believed to be relatively stable and resistant to interference. In a spatial task, the reference memory mimics two aspects of episodic memory, namely the "what" (content) and "where" (place) dimensions of an event.

It is recognized that stereoisomers such as enantiomers of a chiral drug may possess pharmacokinetic and pharmacodynamic properties different from their racemates. There is thus a risk for misinterpretation of drug disposition and plasma drug concentration-effect data generated for a racemic drug using a non-stereoselective assay. The data collected for the racemic form of a drug is frequently both quantitatively and qualitatively inaccurate with respect to the individual enantiomers. For example, the clearance of the unresolved drug may indicate concentration- and time-dependence even though this pharmacokinetic process is concentration- and time-independent for each of the enantiomers.

C. J. Loland et al., Biol. Psychiatry, 2012 Sep. 1, 72 (5), pages 405 to 413 ("R-Modafinil (Armodafinil): A unique dopamine up-take inhibitor and potential medication for psychostimulant abuse"), found out that R-modafinil displays an in vitro profile different from that of cocaine. It was, however, concluded that further trials with R-modafinil as a substitute therapy are warranted.

In WO 03/059873 A1 pharmaceutical compounds are disclosed comprising both a thiazole group and a quaternary carbon comprising three phenyl groups next to a sulfoxide moiety. These compounds shall furnish a medicament which regulates calcium-activated potassium channels and which acts as modulator of Skca and/or Ikca channels. According to this document the proposed pharmaceutical compounds shall be suited for the treatment of diseases or conditions like respiratory diseases such as asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhea, ischemia, cerebral ischemia, ischemic heart disease, angina pectoris, coronary heart disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type 11, hyperinsulinemia, premature labor, baldness, cancer, and immune suppression in particular in for reducing or inhibiting undesired immune-regulatory actions, Addison's disease, alopecia areata, Ankylosing spondylitis, hemolytic anemia (anemia hemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, auto-immune asthma, auto-immune hemolysis, Bechet's disease, Boeck's disease, inflammatory bowel disease, Burkitt's lymphom, Chron's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, auto-immune demyelinating diseases, Dupuytren's contracture, encephalomyelitis, encephalomyelitis allergic, endophthalmia phacoanaphylactica, enteritis allergic, auto-immune enteropathy syndrome, erythema nodosum leprosum, idiopathic facial paralysis, chronic fatigue syndrome, febris rheumatica, glomerulo nephritis, Goodpasture's syndrome, Graves' disease, Hamman-Rich's disease, Hashimoto's disease, Hashimoto's thyroiditis, sudden hearing loss, sensoneural hearing loss, hepatitis chronica, Hodgkin's disease, hemoglobinuria paroxysmatica, hypogonadism, ileitis regionalis, iritis, leucopenia, leukemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgaris, polyarteritis nodosa, polyarthritis chronica primaria, polymyositis, polyradiculitis acuta, psoreasis, purpura, pyoderma gangrenosum, Quervain's thyreoiditis, Reiter's syndrome, sarcoidosis, ataxic sclerosis, progressive systemic sclerosis, scleritis, sclerodermia, multiple sclerosis, sclerosis disseminata, acquired spenic atrophy, infertility due to antispermatozoan antibodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome, virus (AIDS or EBV) associated B cell lymphom, parasitic diseases such as Lesihmania, and immunosuppressed disease states such as viral infections following allograft transplantations, graft vs. Host syndrome, transplant rejection, or AIDS, cancers, chronic active hepatitis diabetes, toxic shock syndrome, food poisoning, and transplant rejection.

US 2002/0183334 is about substituted thioacetamides. The rather broad set of compounds disclosed in US 2002/0183334 shall be suited for the treatment of sleepiness, tiredness, Parkinson's disease, cerebral ischemia, stroke, sleep apneas, eating disorders, attention deficit hyperactivity disorder, cognitive dysfunction, disorders associated with hypofunctionality of the cerebral cortex, depression, schizophrenia, and chronic fatigue syndrome, and also for the promotion of wakefulness, stimulation of appetite, or stimulation of weight gain.

In WO 03/066035 a broad range of thioether sulfonamides is disclosed which shall be suited for the treatment of diabetes mellitus.

US 2005/0234040 refers to tricyclic aromatic and bisphenyl sulfinyl derivatives. The compounds specified in this document shall furnish medicaments suited for the treatment of excessive sleepiness, promotion and/or improvement of wakefulness, preferably improvement of wakefulness in patients with excessive sleepiness associated with narcolepsy, sleep apnea, preferably obstructive sleep apnea/hypopnea, and shift work disorder), Parkinson's disease, Alzheimer's disease, cerebral ischemia, stroke, eating disorders, attention deficit disorder ("ADD"), attention deficit hyperactivity disorder ("ADHD"), depression, schizophrenia, fatigue, preferably fatigue associated with cancer or neurological diseases, such as multiple sclerosis and chronic fatigue syndrome, stimulation of appetite and weight gain and improvement of cognitive dysfunction.

From EP 2 292 213 A1 a pharmaceutical composition consisting of a specific polymorphic form of R-(−)-modafinil and one or more pharmaceutically-acceptable carriers, diluents or excipients can be derived by use of which subjects with narcolepsy can be treated ensuring a longer lasting plasma concentration and higher overall exposure at high doses when compared to equivalent amounts of the racemic form of modafinil.

Although numerous attempts have been made it would be desirable to provide a way which would allow to efficiently and effectively cope with known learning and/or memory deficits. Compounds and methods which exhibit a further improvement of memory and learning functions are still sought. It is therefore an object of the present disclosure to provide agents that increase learning capabilities and memory performance, in particular in aging individuals. It is another object of the present disclosure to treat age-dependent decline of cognitive functions, and to provide an effective agent which can be used for the treatment of age-dependent decline and/or of disorders that in turn require improvement of learning capabilities and memory performance.

BRIEF SUMMARY

Therefore, the present disclosure provides a chemical compound having the general formula (I):

Formula (I)

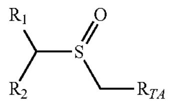

wherein $R_1$ is a phenyl group and $R_2$ is a meta-substituted phenyl group; and $R_{TA}$ is a substituted or unsubstituted thiazole ring wherein substituted means substituted with a residue selected from the group consisting of alkyl, cykloalkyl, heterocycloalkyl, hydroxyalkyl, alkylthio, ether, hydroxyl, fluoride, chloride, bromide and iodide.

It has been found that those compounds according to formula (I) are preferred in which $R_{TA}$ is a 2-1,3-, or 4-1,3- or 5-1,3-thiazole ring with the general Formula Formula (Iia)

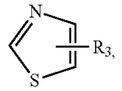

wherein $R_3$ is present on the ring according to Formula (Iia) 1 or 2 times, equal or independently, and wherein $R_3$ is selected from the group consisting of hydrogen, alkyl, cycloalkyl, heterocycloalkyl, alkylamino, in particular dialkylamino, arylamino, in particular diarylamino, hydroxyalkylamino, alkoxy, arylalkyl, hydroxyalkyl, thioalkyl, haloalkyl, haloaryl, haloarylalkyl, haloalkoxy, mono or multi-substituted alkyl, mono or multi-substituted cycloalkyl, mono or multi-substituted heterocycloalkyl, mono or multi-substituted alkylamino, in particular dialkylamino, mono or multi-substituted arylamino, in particular diarylamino, mono or multi-substituted hydroxyalkylamino, mono or multi-substituted alkoxy, mono or multi-substituted arylalkyl, mono or multi-substituted hydroxyalkyl, mono or multi-substituted thioalkyl, mono or multi-substituted haloalkyl, mono or multi-substituted haloaryl, mono or multi-substituted haloarylalkyl, mono or multi-substituted haloalkoxy and carboxylate ester.

It has been found that, additionally or alternatively, those compounds according to formula (I) are preferred in which the meta-substituent of residue $R_2$ is selected from the group consisting of alkyl, cycloalkyl, heterocycloalkyl, alkylamino, in particular dialkylamino, arylamino, in particular diarylamino, hydroxyalkylamino, alkoxy, hydroxyl, carboxylic acid group, carboxylate ester group, halogen, in particular a bromine substituent, arylalkyl, hydroxyalkyl, thioalkyl, haloalkyl, haloaryl, haloarylalkyl, haloalkoxy, mono or multi-substituted alkyl, mono or multi-substituted cycloalkyl, mono or multi-substituted heterocycloalkyl, mono or multi-substituted alkylamino, in particular dialkylamino, mono or multi-substituted arylamino, in particular diarylamino, mono or multi-substituted hydroxyalkylamino, mono or multi-substituted alkoxy, mono or multi-substituted arylalkyl, mono or multi-substituted hydroxyalkyl, mono or multi-substituted thioalkyl, mono or multi-substituted haloalkyl, mono or multi-substituted haloaryl, mono or multi-substituted haloarylalkyl, mono or multi-substituted haloalkoxy and carboxylate ester, wherein substituted means substituted with a residue selected from the group consisting of alkyl, cykloalkyl, heterocycloalkyl, hydroxyalkyl, alkylthio, ether, hydroxyl, fluoride, chloride, bromide and iodide, and/or wherein $R_3$ is hydrogen or alkyl, in particular methyl, or oxyalkyl, in particular oxymethyl, or alkyl substituted with at least one residue selected from the group consisting of heterocycloalkyl, carboxylic acid, amide and ester, in particular methyl substituted with heterocycloalkyl, preferably heterocycloalkyl containing at least two heteroatoms.

Even more preferred in this regard are residues $R_{TA}$ which represent a 2-1,3-thiazole group or a 5-1,3-thiazole group, in particular a 5-1,3-thiazole group.

Heterocycloalkyl is preferably selected from the group consisting of morpholino, piperazino and methylpiperazino.

Aryl, i.e., an aryl group in the meaning of the present disclosure preferably denotes phenyl, and substituted aryl preferably denotes mono or multi-substituted phenyl. Exemplary substituted phenyl include for example -o-$C_6H_4$—R', -m-$C_6H_4$—R' and -p-$C_6H_4$—R', wherein R' is an alkyl as defined herein or as defined for residues $R_3$, $R_4$, $R_5$, $R_6$ and $R_7$. Fused aryl in the meaning of the present disclosure preferably denotes an aromatic ring being fused with at least one aromatic ring system, the fused aryl group in particular being made of five to 15 carbon atoms, e.g., naphthyl and anthracenyl. These fused aryl may also be mono or multi-substituted, e.g., 1-naphthyl, 2-naphthyl, 1-anthracenyl or 2-anthracenyl, as defined herein.

Heteroaryl, i.e., a heteroaryl group in the meaning of the present disclosure preferably denotes a 3 to 8-membered heterocyclic aromatic group which contains at least one heteroatom selected from the group consisting of O, N, and S. Heteroaryl in the meaning of the present disclosure also includes a heteroaryl ring being fused to another aromatic ring. Both heteroaryl and fused heteroaryl group can also be mono or multi-substituted as defined herein.

Alkyl, i.e., an alkyl group in the meaning of the present disclosure preferably comprises an alkyl, alkenyl and alkynyl residue, in particular a $C_1$-$C_6$-alkyl, $C_2$-$C_6$-alkenyl and $C_2$-$C_6$-alkynyl residue. Suitable residues are selected from the group consisting of $-CH_3$, $-C_2H_5$, $-CH{=}CH_2$, $-C{\equiv}CH$, $-C_3H_7$, $-CH(CH_3)_2$, $-CH_2-CH{=}CH_2$, $-C(CH_3){=}CH_2$, $-CH{=}CH-CH_3$, $-C{\equiv}C-CH_3$, $-CH_2-C{\equiv}CH$, $-C_4H_9$, $-CH_2-CH(CH_3)_2$, $-CH(CH_3)-C_2H_5$, $-C(CH_3)_3$, $-C_5H_{11}$, $-C_6H_{13}$, $-C(R')_3$, $-C_2(R')_5$, $-CH_2-C(R')_3$, $-C_3(R')_7$, $-C_2H_4-C(R')_3$, $-C_2H_4-CH{=}CH_2$, $-CH{=}CH-C_2H_5$, $-CH{=}C(CH_3)_2$, $-CH_2-CH{=}CH-CH_3$, $-CH{=}CH-CH{=}CH_2$, $-C_2H_4-C{\equiv}CH$, $-C{\equiv}C-C_2H_5$, $-CH_2-C-C{\equiv}CH_3$, $-C{\equiv}C-CH{=}CH_2$, $-CH{=}CH-C{\equiv}CH$, $-C{\equiv}C-C{\equiv}CH$, $-C_2H_4-CH(CH_3)_2$, $-CH(CH_3)-C_3H_7$, $-CH_2-CH(CH_3)-C_2H_5$, $-CH(CH_3)-CH(CH_3)_2$, $-C(CH_3)_2-C_2H_5$, $-CH_2-C(CH_3)_3$, $-C_3H_6-CH{=}CH_2$, $-CH{=}CH-C_3H_7$, $-C_2H_4-CH{=}CH-CH_3$, $-CH_2-CH{=}CH-C_2H_5$, $-CH_2-CH{=}CH-CH{=}CH_2$, $-CH{=}CH-CH{=}CH-CH_3$, $-CH{=}CH-CH_2-CH{=}CH_2$, $-C(CH_3){=}CH-CH{=}CH_2$, $-CH{=}C(CH_3)-CH{=}CH_2$, $-CH{=}CH-C(CH_3){=}CH_2$, $-CH_2-CH{=}C(CH_3)_2$, $C(CH_3){=}C(CH_3)_2$, $-C_3H_6-C{\equiv}CH$, $-C{\equiv}C-C_3H_7$, $-C_2H_4-C{\equiv}C-CH_3$, $-CH_2-C-C{\equiv}C_2H_5$, $-CH_2-C-C{\equiv}CH{=}CH_2$, $-CH_2-CH{=}CH-C{\equiv}CH$, $-CH_2-C-C{\equiv}C-CH$, $-C{\equiv}C-CH{=}CH-CH_3$, $-CH{=}CH-C-C{\equiv}CH_3$, $-C-C{\equiv}C-C{\equiv}CH_3$, $-C{\equiv}C-CH_2-CH{=}CH_2$, $-CH{=}CH-CH_2-C{\equiv}CH$, $-C{\equiv}C-CH_2-C{\equiv}CH$, $-C(CH_3){=}CH-CH{=}CH_2$, $-CH{=}C(CH_3)-CH{=}CH_2$, $-CH{=}CH-C(CH_3){=}CH_2$, $-C(CH_3){=}CH-C{\equiv}CH$, $-CH{=}C(CH_3)-C{\equiv}CH$, $-C{\equiv}C-C(CH_3){=}CH_2$, $-C_3H_6-CH(CH_3)_2$, $-C_2H_4-CH(CH_3)-C_2H_5$, $-CH(CH_3)-C_4H_9$, $-CH_2-CH(CH_3)-C_3H_7$, $-CH(CH_3)-CH_2-CH(CH_3)_2$, $-CH(CH_3)-CH(CH_3)-C_2H_5$, $-CH_2-CH(CH_3)-CH(CH_3)_2$, $-CH_2-C(CH_3)_2-C_2H_5$, $-C(CH_3)_2-C_3H_7$, $-C(CH_3)_2-CH(CH_3)_2$, $-C_2H_4-C(CH_3)_3$, $-CH(CH_3)-C(CH_3)_3$, $-C_4H_8-CH{=}CH_2$, $-CH{=}CH-C_4H_9$, $-C_3H_6-CH{=}CH-CH_3$, $-CH_2-CH{=}CH-C_3H_7$, $-C_2H_4-CH{=}CH-C_2H_5$, $-CH_2-C(CH_3){=}C(CH_3)_2$, $-C_2H_4-CH{=}C(CH_3)_2$, $-C_4H_8-C{\equiv}CH$, $-C{\equiv}C-C_4H_9$, $-C_3H_6-C-C{\equiv}CH_3$, $-CH_2-C-C{\equiv}C_3H_7$, and $-C_2H_4-C-C{\equiv}C_2H_5$;

wherein R' can be defined as residue $R_3$ as outlined above for formula (I). R' as referred to above preferably is hydrogen, methyl, ethyl, n-propyl, i-propyl, n-butyl, tert-butyl, sec-butyl or isobutyl, in particular hydrogen, methyl or i-propyl.

The alkyl group according to one preferred embodiment of formula (I), in particular for residue $R_3$, is methyl, ethyl, propyl, isopropyl, n-butyl, tert-butyl, sec-butyl, and isobutyl, preferably methyl or isopropyl, and more preferably alkyl is selected from the group consisting of methyl, ethyl, iso-propyl, and tert-butyl.

Arylalkyl, i.e., an arylalkyl group in the meaning of the present disclosure preferably denotes a linear or branched $C_1$-$C_6$-alkyl substituted with at least one aryl group as defined above, preferably benzyl or phenylethyl. Suitable mono or multi-substituted arylalkyl comprise for example 4-hydroxybenzyl, 3-fluorobenzyl or 2-fluorophenylethyl.

Cycloalkyl, i.e., a cycloalkyl group in the meaning of the present disclosure preferably denotes a non-aromatic ring system containing three to eight carbon atoms, preferably four to eight carbon atoms. With mono or multi-substituted cycloalkyl one or more of the carbon atoms in the ring may be substituted by a group R' as defined above, preferably methyl, ethyl, n-propyl, i-propyl, n-, i- or t-butyl. Suitable $C_3$-$C_8$-cycloalkyl groups can be selected from the group consisting of -cyclo-$C_3H_5$, -cyclo-$C_4H_7$, -cyclo-$C_5H_9$, -cyclo-$C_6H_{11}$, -cyclo-$C_7H_{13}$, and -cyclo-$C_8H_{15}$.

Heterocycloalkyl, i.e., heterocycloalkyl group in the meaning of the present disclosure preferably denotes a non-aromatic carbon ring system in which one or more ring carbon atoms have been replaced by a heteroatom functional group such as O, S, SO, $SO_2$, N, or NR'2, wherein R' is defined as outlined above. Preferred heterocycloalkyl groups can be selected from the group consisting of morpholine-4-yl, piperazinyl, and 1-alkylpiperazine-4-yl.

Hydroxyalkyl, i.e., a hydroxyalkyl group in the meaning of the present disclosure preferably denotes a hydroxyalkyl group in which the alkyl group is defined as outlined above, preferably methyl, ethyl, n-propyl, i-propyl, n-, i- or t-butyl. Suitable hydroxyalkyl groups are selected from the groups consisting of a hydroxymethyl, hydroxyethyl, hydroxypropyl, and hydroxy-iso-propyl group. The hydroxyalkyl group according to a preferred embodiment of formula (I) is hydroxymethyl. Once bonded the alkyl or methyl group may also be denoted as alkylene or methylene group, respectively.

Alkylthio, i.e., an alkylthio group in the meaning of the present disclosure preferably denotes an alkylthio group in which the alkyl group is defined as outlined above, preferably for $R_3$, in particular thiomethyl.

Haloalkyl, i.e., a haloalkyl group in the meaning of the present disclosure preferably denotes a haloalkyl group in which the alkyl group is defined as outlined above, in particular for $R_3$, and wherein said alkyl is substituted by one or more halogen atoms, preferably substituted by one to five halogen atoms, in particular by fluor or chlorine atoms. In a preferred embodiment the haloalkyl group is selected from the group consisting of $—C(R^{10})_3$, $—CR^{10}(R^{10'})_2$, $—CR^{10}(R^{10'})R^{10''}$, $—C_2(R^{10})_5$, $—CH_2—C(R^{10})_3$, $—C(R^{10'})_2—CH(R^{10'})_2$, $—CH_2—CR^{10}(R^{10'})_2$, $—CH_2—CR^{10}(R^{10'})R^{10''}$, $—C_3(R^{10})_7$, or $—C_2H_4—C(R^{10})_3$, wherein $R^{10}$, $R^{10'}$, $R^{10''}$ represent F, Cl, Br or I, preferably F.

Haloaryl, i.e., a haloaryl group in the meaning of the present disclosure preferably denotes a haloaryl group in which at least one aromatic carbon atom is substituted by one or more halogen atoms, preferably substituted by one to five halogen atoms. Preferably, halogen atoms are selected from the group consisting of fluorine, chlorine and bromine atoms, and preferably fluorine.

Haloarylalkyl, i.e., a haloarylalkyl group in the meaning of the present disclosure preferably denotes a haloarylalkyl group in which the arylalkyl group is defined as outlined above and wherein at least one aromatic carbon atom of said aryl group is substituted by one or more halogen atoms, preferably substituted by one to five halogen atoms. Preferably, halogen atoms are selected from the group consisting of fluorine, chlorine, bromine and iodine atoms, more preferably from fluorine and chlorine atoms.

Haloalkoxy, i.e., a haloalkoxy group in the meaning of the present disclosure preferably denotes a haloalkoxy group in which the alkoxy group is defined as outlined above and wherein said alkoxy is substituted by one or more halogen atoms, preferably substituted by one to five halogen atoms, in particular by fluorine, chlorine, bromine and/or iodine atoms, more preferably fluorine and/or chlorine atoms. Preferably, the haloalkoxy group is selected from the group consisting of $—OC(R^{10})_3$, $—OCR^{10}(R^{10'})_2$, $—OCR' (R^{10'}) R^{10''}$, $—OC_2(R^{10})_5$, $—OCH_2—C(R^{10})_3$, $—OCH_2—CR^{10}(R^{10'})_2$, $—OCH_2—CR^{10}(R^{10'})R^{10''}$, $—OC_3(R^{10})_7$ or $—OC_2H_4—C(R^{10})_3$, wherein $R^{10}$, $R^{10'}$, $R^{10''}$ represent F, Cl, Br or I, preferably F.

Alkylamino, i.e., an alkylamino group in the meaning of the present disclosure preferably denotes an alkylamino group in which the alkyl group is defined as outlined above, in particular for $R_3$. The alkylamino group in the meaning of the present disclosure preferably denotes a $(alkyl)_2$-N-group, i.e., a dialkylamino group, or a alkyl-NH— group. The dialkylamino group is preferred. Alkyl is preferably defined as outlined above.

Arylamino, i.e., a diarylamino group in the meaning of the present disclosure preferably denotes an arylamino group in which the aryl group is defined as outlined above. The arylamino group denotes a $(aryl)_2$-N-group, i.e., a diarylamino group, or a aryl-NH— group. The diarylamino group is preferred, in particular the diphenylamino group. Aryl is preferably defined as outlined above.

Hydroxyalkylamino, i.e., an hydroxyalkylamino group in the meaning of the present disclosure preferably denotes an hydroxyalkylamino group in which the alkyl group is defined as outlined above, in particular for $R_3$, and wherein the hydroxyalkylamino group denotes a $(HO\text{-}alkyl)_2$-N-group or a HO-alkyl-NH— group, or a (HO-alkyl)-N-(alkyl)- group. Alkyl is preferably defined as outlined above.

Compounds having infinite chains consisting for instance of repeating $R_1$, $R_2$, $R_3$ units and the like are not encompassed by this disclosure.

Constituents which are optionally substituted as stated herein, may be substituted, unless otherwise noted, at any chemically possible position.

Moreover, those diastereomerically enriched or a diastereomerically pure chemical compounds according to formula (I) furnish particularly improved results in terms of learning capabilities, in particular spatial learning capabilities, and/or memory functions, in particular reference memory, in particular by use of those compounds according to formula (I) in which $R_{TA}$ is a 2-1,3-, or 4-1,3- or 5-1,3-thiazole ring with the general Formula (IIa).

Those compounds according to formula (I) are particularly preferred in which $R_2$ is a phenyl ring having a chlorine, bromine or iodine substituent, in particular a bromine substituent, in meta-position.

In another preferred embodiment the compound according to formula (I) is a diastereomeric mixture of 5-((((R),(R)-3-halophenyl)(phenyl)methyl)sulfinyl)methyl)thiazole, in particular 5-((((R),(R)-3-bromophenyl)(phenyl)methyl)sulfinyl)methyl)thiazole and more in particular 5-((((R),(R)-3-bromophenyl)(phenyl)methyl)sulfinyl)methyl)-1,3-thiazole, 5-((((R),(S)-3-halophenyl)(phenyl)methyl)sulfinyl)methyl)thiazole, in particular 5-((((R),(S)-3-bromophenyl)(phenyl)methyl)sulfinyl)methyl)thiazole and more in particular 5-((((R),(S)-3-bromophenyl)(phenyl)methyl)sulfinyl)methyl)-1,3-thiazole, 5-((((S),(R)-3-halophenyl)(phenyl)methyl)sulfinyl)methyl)thiazole, in particular 5-((((S),(R)-3-bromophenyl)(phenyl)methyl)sulfinyl)methyl)thiazole and more in particular 5-((((S),(R)-3-bromophenyl)(phenyl)methyl)sulfinyl)methyl)-1,3-thiazole, and 5-((((S),(S)-3-halophenyl)(phenyl)methyl)sulfinyl)methyl)thiazole, in particular 5-((((S),(S)-3-bromophenyl)(phenyl)methyl)sulfinyl)methyl)thiazole and more in particular 5-((((S),(S)-3-bromophenyl)(phenyl)methyl)sulfinyl)methyl)-1,3-thiazole.

In another preferred embodiment the compound according to formula (I) represents a diastereomeric mixture enriched in 5-((((S),(S)-3-halophenyl)(phenyl)methyl)sulfinyl)methyl)thiazole, in particular enriched in 5-((((S),(S)-3-bromophenyl)(phenyl)methyl)sulfinyl)methyl)thiazole and more in particular enriched in 5-((((S),(S)-3-bromophenyl)(phenyl)methyl)sulfinyl)methyl)-1,3-thiazole.

Even more preferred, the compound according to formula (I) is an essentially diastereomerically pure chemical compound of one of the four diastereomers having the general formula (I), in particular 5-((((S),(S)-3-halophenyl)(phenyl)methyl)sulfinyl)methyl)thiazole, more in particular 5-((((S),(S)-3-bromophenyl)(phenyl)methyl)sulfinyl)methyl)thiazole and even more in particular 5-((((S),(S)-3-bromophenyl)(phenyl)methyl)sulfinyl)methyl)-1,3-thiazole, i.e., it is essentially free of any 5-((((R),(R)-3-bromophenyl)(phenyl)methyl)sulfinyl)methyl)-1,3-thiazole, in particular of any 5-((((R),(R)-3-bromophenyl)(phenyl)methyl)sulfinyl)methyl)thiazole, 5-((((R),(S)-3-bromophenyl)(phenyl)methyl)sulfinyl)methyl)-1,3-thiazole, in particular of any 5-((((R),(S)-3-bromophenyl)(phenyl)methyl)sulfinyl)methyl)thiazole, and 5-((((S),(R)-3-bromophenyl)(phenyl)methyl)sulfinyl) methyl)-1,3-thiazole, in particular of any 5-((((S),(R)-3-bromophenyl)(phenyl)methyl)sulfinyl)methyl)thiazole.

Accordingly, the compound according to formula (I) preferably is 5-((((S),(S)-3-bromophenyl)(phenyl)methyl) sulfinyl)methyl)thiazole, and even more preferably 5-((((S),(S)-3-bromophenyl)(phenyl)methyl)sulfinyl) methyl)-1,3-thiazole. The latter compound can also be depicted by way of the following formula:

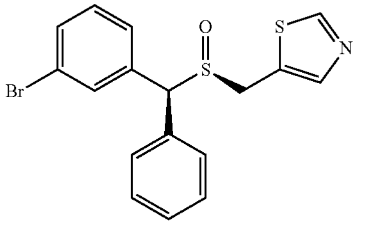 [SMILES: O=[S@@](Cc1cncs1)[C@@H](c1ccccc1)c1cccc(Br)c1]

It has been found that most promising results in particular in terms of an improved spatial memory, in particular with aging individuals or those individuals suffering age-related cognitive decline, can be obtained when the compound according to formula (I) is 5-((((S),(S)-3-halophenyl)(phenyl)methyl)sulfinyl)methyl)thiazole, in particular 5-((((S),(S)-3-bromophenyl)(phenyl)methyl)sulfinyl) methyl)thiazole and more in particular 5-((((S),(S)-3-bromophenyl)(phenyl)methyl)sulfinyl)methyl)-1,3-thiazole.

Alternatively, also diastereomerically mixtures enriched in 5-((((S),(S)-3-halophenyl)(phenyl)methyl)sulfinyl) methyl)thiazole, in particular 5-((((S),(S)-3-bromophenyl) (phenyl)methyl)sulfinyl)methyl)thiazole and more in particular 5-((((S),(S)-3-bromophenyl)(phenyl)methyl)sulfinyl) methyl)-1,3-thiazole can be employed containing 5-((((R), (R)-3-bromophenyl)(phenyl)methyl)sulfinyl)methyl) thiazole, 5-((((R),(S)-3-bromophenyl)(phenyl)methyl) sulfinyl)methyl)thiazole and/or 5-((((S),(R)-3-bromophenyl)(phenyl)methyl)sulfinyl)methyl)thiazole.

In general with the present disclosure compounds of formula (I) as defined herein are provided for use in therapy, i.e., for use as a medicament, and in particular for treating age-related cognitive decline, more in particular for treating age-related cognitive decline according to 2018 ICD-10-CM Diagnosis Code R41.81, e.g., according to the US version of 2018 ICD-10-CM Diagnosis Code R41.81.

It is of particular interest that with the compounds of formula (I), preferably diastereomerically pure 5-((((S),(S)-3-halophenyl)(phenyl)methyl)sulfinyl)methyl)thiazole, in particular 5-((((S),(S)-3-bromophenyl)(phenyl)methyl)sulfinyl)methyl)thiazole and more in particular 5-((((S),(S)-3-bromophenyl)(phenyl)methyl)sulfinyl)methyl)-1,3-thiazole, or a diastereomeric mixture being enriched in 5-((((S),(S)-3-halophenyl)(phenyl)methyl)sulfinyl)methyl)thiazole, in particular 5-((((S),(S)-3-bromophenyl)(phenyl)methyl)sulfinyl)methyl)thiazole and more in particular 5-((((S),(S)-3-bromophenyl)(phenyl)methyl)sulfinyl)methyl)-1,3-thiazole improvements in terms of learning capabilities, in particular spatial learning capabilities, and memory performance, in particular reference memory, can be accomplished with human individuals who do not have memory deficits and/or cognitive defects.

Accordingly, these results can also be obtained with individuals who do not have reference memory deficits and/or cognitive defects caused by diseases of the brain. The compounds according to the present disclosure can thus also be administered to and are also effective with healthy individuals to improve reference memory, and/or other cognitive abilities such as learning capabilities (or to overcome respective deficits). Accordingly, the present disclosure therefore also relates to the use of a compound according to the present disclosure for the improvement of learning capabilities, in particular spatial learning capabilities, and memory performance, in particular reference memory, in healthy individuals, in particular in healthy aging individuals.

In addition, the present disclosure also relates to the use of a compound according to the present disclosure for the improvement of learning capabilities, in particular spatial learning capabilities, and memory performance, in particular reference memory with human individuals who have reference memory deficits and/or cognitive defects, in particular reference memory deficits, caused by diseases of the brain. In this regard, a patient can be treated with the compounds according to formula (I), who has reference memory deficits and/or cognitive defects, in particular and/or reference memory deficits, caused by Alzheimer; Down syndrome; vascular cognitive impairment; stroke; frontotemporal dementia; behavioural, semantic or progressive aphasia type dementia; dementia with Lewy bodies; subcortical dementias; Parkinson's disease dementia; alcohol related dementia; dementia caused by traumatic brain injury; Huntington's disease related dementia; AIDS-related dementia; attention deficit disorders; or schizophrenia, or who has any form of cognitive impairment.

The compound according to formula (I) of the present disclosure, in particular 5-((((S),(S)-3-bromophenyl)(phenyl)methyl)sulfinyl)methyl)thiazole, can be used alone or in combination with other cognitive enhancing compounds such as rivastigmin, donepezil, galanthamin, clozapine, risperidone, memantine, olanzapine, aripiprazole, quitiapine, clozapine, D1 agonists, nicotinic alfa 7-agonists, d-serine, d-cycloserine. PDE2, 4,9 inhibitors, AMPA agonists, lamotrigine, n-desmethylclozapine, mGlu receptor agonists, GABA A receptor agonists, muscarinic 1 and 4 receptor agonists, to treat lack of cognitive impairments and improve reference memory.

The compounds according to the present disclosure are particularly useful for treating patients having learning deficits and/or memory deficits, in particular spatial learning and memory task deficits, due to particular demands in healthy and aging individuals, diseases of the brain, mental disorders or cognitive deficits, especially patients having Alzheimer, Down syndrome, stroke (vascular cognitive impairment), frontotemporal dementia, behavioural, semantic and progressive aphasia type dementia, dementia with Lewy bodies, subcortical dementias, and Parkinson's disease dementia, alcohol related dementia, dementia caused by traumatic brain injury, Huntington's disease related dementia, AIDS-related dementia, attention deficit disorders; or schizophrenia.

The compound according to formula (I), preferably 5-((((S),(S)-3-bromophenyl)(phenyl)methyl)sulfinyl) methyl)thiazole, more preferably 5-((((S),(S)-3-bromophenyl)(phenyl)methyl)sulfinyl)methyl)-1,3-thiazole can be administered to a patient having or being at risk to develop any of the disorders referred to above in an effective amount. It is also possible to administer the compound to healthy individuals for improving learning capabilities and/or memory performance, in particular reference memory, and more preferably spatial learning capabilities and reference memory.

DETAILED DESCRIPTION

Figure 1:
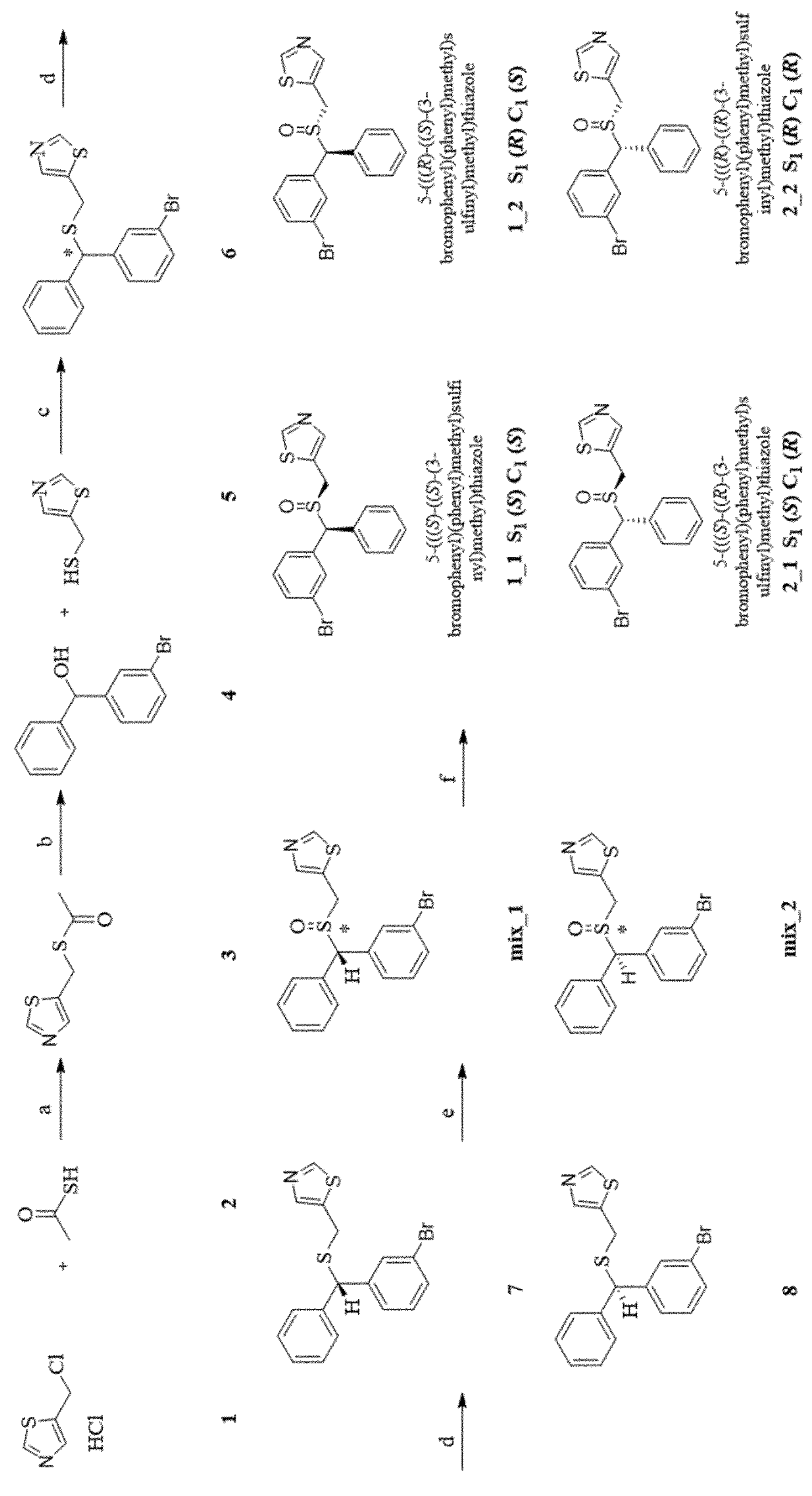
FIG. 1 depicts the synthesis of the diastereomers of 5-((((3-bromophenyl)(phenyl)methyl)sulfinyl)methyl)thiazole.

According to a preferred embodiment, it is convenient to administer the compound according to the present disclosure, in particular 5-((((S),(S)-3-bromophenyl)(phenyl) methyl)-sulfinyl)methyl)thiazole, more in particular 5-((((S),(S)-3-bromophenyl)(phenyl)methyl)sulfinyl) methyl)-1,3-thiazole, by a single dosage unit form, especially as a capsule or a tablet. A preferred formulation comprises a soft gelatin capsule containing at least one compound according to formula (I) dissolved in oil within the capsule with one or more emulsifying agents. Accordingly, gelatin capsules are preferred which comprise one or more emulsifying agents and also at least one compound according to formula (I) dissolved in at least one oil.

Preferred dosages comprise administration dosages of about 1 mg/kg to about 25 mg/kg body weight. Suitable dosage forms also comprise formulations comprising at least one compound according to formula (I) in an amount of about 0.1 mg to about 10 g, preferably of about 1 mg to about 1 g, and more preferably of about 10 mg to about 200 mg.

According to a preferred embodiment, the compound of formula (I) according to the present disclosure, in particular 5-((((S),(S)-3-bromophenyl)(phenyl)methyl)sulfinyl) methyl)thiazole, more in particular 5-((((S),(S)-3-bromophenyl)(phenyl)methyl)sulfinyl)methyl)-1,3-thiazole, can be part of formulations which contain at least or can be administered with one or more compounds, also referred to as co-agents, selected from the group consisting of Rivastigmin, Donepezil, Galanthamin, clozapine, risperidone, memantine, olanzapine, aripiprazole, quitiapine, clozapine, D1 agonists, nicotinic alfa 7, agonists, d-serine, d-cycloserine, PDE2,4,9 inhibitors, AMPA agonists, Lamotrigine, n-desmethylclozapine, mGlu receptor agonists, GABA A receptor agonists, and Muscarinic 1 and 4 agonists or other potential cognitive enhancing compounds.

The object of the present disclosure has also been solved by the use of a compound according to formula (I), in particular 5-((((S),(S)-3-bromophenyl)(phenyl)methyl)sulfinyl)-methyl)thiazole, more in particular 5-((((S),(S)-3-bromophenyl)(phenyl)methyl)sulfinyl)methyl)-1,3-thiazole, in the manufacture of a medicament for the improvement of learning capabilities, in particular spatial learning capabilities, and memory performance, in particular reference memory, and more in particular spatial learning capabilities and reference memory.

According to another aspect of the present disclosure the compound according to formula (I), in particular 5-((((S),(S)-3-halophenyl)(phenyl)methyl)sulfinyl)methyl) thiazole, more in particular 5-((((S),(S)-3-bromophenyl) (phenyl)methyl)sulfinyl)methyl)thiazole and even more in particular 5-((((S),(S)-3-bromophenyl)(phenyl)methyl)sulfinyl)methyl)-1,3-thiazole, has been found for use in, in particular selectively, inhibiting DAT-mediated dopamine reuptake in the synapses in the brain of a mammal, in particular a human individual, and also in the manufacture of a medicament for inhibiting DAT-mediated dopamine reuptake in the synapses in the brain of a mammal, in particular of a human individual. With the compounds according to formula (I), in particular 5-((((S),(S)-3-halophenyl)(phenyl)methyl)sulfinyl)methyl)thiazole, more in particular 5-((((S),(S)-3-bromophenyl)(phenyl)methyl)sulfinyl)methyl)thiazole and even more in particular 5-((((S),(S)-3-bromophenyl)(phenyl)methyl)sulfinyl)methyl)-1,3-thiazole, inhibition of DAT is not only highly effective but also highly specific over SERT and NET inhibition. DAT inhibition with high specificity can be accomplished with the compounds according to formula (I), in particular 5-((((S),(S)-3-halophenyl)(phenyl)methyl)sulfinyl)methyl) thiazole, more in particular 5-((((S),(S)-3-bromophenyl) (phenyl)methyl)sulfinyl)methyl)thiazole and even more in particular 5-((((S),(S)-3-bromophenyl)(phenyl)methyl)sulfinyl)methyl)-1,3-thiazole, at an IC50 of not more than 7.5 μM, in particular of not more than 4.5 μM, more in particular of not more than 2.5 μM, even more in particular of not more than 1.75 μM, and more preferably of not more than 1.0 μM. With 5-((((S),(S)-3-halophenyl)(phenyl)methyl)sulfinyl) methyl)thiazole, in particular 5-((((S),(S)-3-bromophenyl) (phenyl)methyl)sulfinyl)methyl)thiazole and more in particular 5-((((S),(S)-3-bromophenyl)(phenyl)methyl)sulfinyl) methyl)-1,3-thiazole, specific DAT inhibition can even be accomplished at concentrations of not more than 0.75 μM, preferably of not more than 0.5 μM and even more preferably of not more than 0.3 μM. Measurements are based on using an in vitro reuptake inhibition assay (as specified in the experimental section).

It has surprisingly been found that 5-((((S),(S)-3-halophenyl)(phenyl)methyl)sulfinyl)methyl)thiazole, in particular 5-((((S),(S)-3-bromophenyl)(phenyl)methyl)sulfinyl) methyl)thiazole and more in particular 5-((((S),(S)-3-bromophenyl)(phenyl)methyl)sulfinyl)methyl)-1,3-thiazole is at least 5 times, in particular at least 8 times and more in particular at least 10 times as effective in selectively inhibiting DAT-mediated dopamine reuptake in the synapses in the brain as 5-((((R),(R)-3-bromophenyl)(phenyl)methyl) sulfinyl)methyl)-1,3-thiazole, 5-((((R),(S)-3-bromophenyl) (phenyl)methyl)sulfinyl)methyl)-1,3-thiazole, 5-((((S),(R)-3-bromophenyl)(phenyl)methyl)sulfinyl)methyl)-1,3-thiazole, and (S)-5-(diphenylmethanesulfinylmethyl)-1,3-thiazole.

Moreover, the object of the present disclosure has also been solved by a pharmaceutical preparation, also referred to herein by pharmaceutical composition, comprising at least one compound according to formula (I), in particular 5-((((S),(S)-3-halophenyl)(phenyl)methyl)sulfinyl)methyl) thiazole, more in particular 5-((((S),(S)-3-bromophenyl) (phenyl)methyl)sulfinyl)methyl)thiazole and even more in particular 5-((((S),(S)-3-bromophenyl)(phenyl)methyl)sulfinyl)methyl)-1,3-thiazole, and at least one pharmaceutically acceptable carrier and/or diluent. Thus, according to another aspect, the present disclosure relates to a pharmaceutical preparation comprising a compound according to the present disclosure and a pharmaceutically acceptable carrier or diluent.

Pharmaceutical "carriers," "diluents" as well as "excipients" are substances to be admixed in a pharmaceutical composition as auxiliary substances to the compound according to the present disclosure or other compounds with pharmaceutical effect (e.g., that have also neurological or behavioural effects). These auxiliary substances do not have a pharmaceutical effect on their own (they are no "active substance" per se) but may assist to optimize the effectivity of the compound according to the present disclosure. The substances used as "carriers," "diluents" and excipients" can often be used interchangeably (i.e., that substances that are used as "diluents" may also serve as "excipients" and/or "carriers").

In general, "carriers" are substances that improve the delivery and the effectiveness of drugs; "diluents" are substances that dilute the active substance in a pharmaceutical preparation; "excipients" are substances that are admixed to the pharmaceutical formulation for defining its releasing properties.

All such "carriers," "diluents" and "excipients" (i.e., auxiliary substances, sometimes also the term "excipient" is used as the general term including all such substances) are, as already stated, inactive substances formulated alongside the active ingredient ("API") of a medication, for the purpose of bulking-up formulations that contain potent active ingredients (thus often also referred to as "bulking agents," "fillers," or "diluents"). Bulking up allows convenient and accurate dispensation of a drug substance when producing a dosage form. They also can serve various therapeutic-enhancing purposes, such as facilitating drug absorption or solubility, or other pharmacokinetic considerations. Such substances can also be useful in the manufacturing process, to aid in the handling of the active substance concerned such as by facilitating powder flowability or non-stick properties, in addition to aiding in vitro stability such as prevention of denaturation over the expected shelf life. The selection of appropriate excipients, carriers and diluents also depends upon the route of administration and the dosage form, as well as the active ingredient and other factors. Such substances, e.g., serve as antiadherents, binders, coatings, disintegrants, fillers, flavors, colors, lubricants, glidants, sorbents, preservatives, sweeteners, etc.

Drug "carriers" are substances that serve as mechanisms to improve the delivery and the effectiveness of drugs. Drug carriers are usually used in sundry drug delivery systems such as: controlled-release technology to prolong in vivo drug actions; decrease drug metabolism, and reduce drug toxicity.

Carriers are generally also used in designs to increase the effectiveness of drug delivery to the target sites of pharmacological actions.

Drug "diluents" are usually substances that simply dilute or reconstitute a pharmaceutical composition (e.g., after storage in dry form).

The pharmaceutical composition with the at least one compound according to formula (I), in particular 5-((((S),(S)-3-halophenyl)(phenyl)methyl)sulfinyl)methyl) thiazole, more in particular 5-((((S),(S)-3-bromophenyl) (phenyl)methyl)sulfinyl)methyl)thiazole and even more in particular 5-((((S),(S)-3-bromophenyl)(phenyl)methyl)sulfinyl)methyl)-1,3-thiazole, usually comprises said compound in an amount of about 0.01 (% w/w) to about 80 (% w/w) in a solid composition or about 0.001 (% w/v) to about 80 (% w/v) in a liquid composition. Preferably the compound according to the present disclosure is present in an amount of about 0.1 (% w/w) to about 50 (% w/w) in a solid composition or about 0.01 (% w/v) to about 10 (% w/v) in a liquid composition, especially of about 1 (% w/w) to about 0 (% w/w) in a solid composition or about 0.1 (% w/v) to about 5 (% w/v) in a liquid composition.

As already stated, preferably, the compounds according to formula (I), in particular 5-((((S),(S)-3-halophenyl)(phenyl) methyl)sulfinyl)methyl)thiazole, more in particular 5-((((S),(S)-3-bromophenyl)(phenyl)methyl)sulfinyl) methyl)thiazole and even more in particular 5-((((S),(S)-3-bromophenyl)(phenyl)methyl)sulfinyl)methyl)-1,3-thiazole, are provided as a pharmaceutical composition, especially as a pharmaceutical single unit dosage form. Pharmaceutical compositions and single unit dosage forms provided herein comprise a prophylactically or therapeutically effective amount of one or more compounds according to formula (I) and optionally also one or more additional prophylactic or therapeutic agents (e.g., in particular a compound provided herein, or other prophylactic or therapeutic agent), and one or more pharmaceutically acceptable carriers or excipients or diluents. In a specifically preferred embodiment and in this context, the term "pharmaceutically acceptable" means approved by a regulatory agency of the Federal or a state government or listed in the European or U.S. Pharmacopeia or other generally recognized pharmacopeia for use in animals, and more particularly in humans.

The term "carrier" refers in one embodiment to a diluent, adjuvant (e.g., Freund's adjuvant (complete and incomplete)), or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions.

In one embodiment, pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form usually depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Examples of suitable excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions provided herein is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, PA), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants can be used in the compositions of the present disclosure to provide solid dosage forms such as tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Suitable disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Suitable lubricants that can be used in pharmaceutical compositions and dosage forms include, but are not limited to, calcium stearate, magnesium stearate, mineral oil, light mineral oil, glycerin27uetiapin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, MD), a coagulated aerosol of synthetic silica (marketed by Degussa Co. of Piano, TX), CAB-O-SIL (a pyrogenic silicon dioxide product sold by Cabot Co. of Boston, MA), and mixtures thereof. If used at all, lubricants are typically used in an amount of less than about 1 weight percent of the pharmaceutical compositions or dosage forms into which they are incorporated.

The active ingredients described herein such as the compounds according to formula (I) and/or the co-agents provided herein can be administered by controlled release means or by delivery devices that are well known to those of ordinary skill in the art. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients. Thus provided are single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral dosage forms can be administered to patients by various routes including, but not limited to, oral, subcutaneous, intravenous (including bolus injection), intramuscular, and intra-arterial. Because their administration typically bypasses patients' natural defenses against contaminants, parenteral dosage forms are in certain embodiments sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

According to a preferred embodiment, the pharmaceutical preparation of the present disclosure further comprises one or more compounds selected from the group consisting of Rivastigmin, Donepezil, Galanthamin, clozapine, risperidone, memantine, olanzapine, aripiprazole, quitiapine, clozapine, D1 agonists, nicotinic alfa 7, agonists, d-serine, d-cycloserine, PDE2,4,9 inhibitors, AMPA agonists, Lamotrigine, n-desmethylclozapine, mGlu receptor agonists, GABA A receptor agonists, and Muscarinic 1 and 4 agonists or other potential cognitive enhancing compounds, agents.

Preferred dosages of the compound according to formula (I), in particular 5-((((S),(S)-3-bromophenyl)(phenyl) methyl)sulfinyl)methyl)thiazole, are 0.1 mg to 10 g, preferably of 1 mg to 1 g, especially 10 mg to 200 mg, of the compound according to the present disclosure. As already stated, the disclosure relates to the use of a composition according to formula (I) for the manufacture of a medicament. And, the disclosure also relates to the use of a composition comprising at least one compound according to formula (I) for the manufacture of a remedy, i.e., pharmacological treatment or prevention of cognitive impairment, dementia and/or reference memory deficits.

The compound of the formula (I), in particular 5-((((S),(S)-3-halophenyl)(phenyl)methyl)sulfinyl)methyl) thiazole, more in particular 5-((((S),(S)-3-bromophenyl) (phenyl)methyl)sulfinyl)methyl)thiazole and even more in particular 5-((((S),(S)-3-bromophenyl)(phenyl)methyl)sulfinyl)methyl)-1,3-thiazole, can be administered to humans, rodents other mammals, as therapeutics per se, and as mixtures with one another or in the form of pharmaceutical preparations which allow enteral or parenteral use and which as active constituent contain an effective dose of the compound of formula (I). The effective dose range can easily be adapted to the severity and the need of the individual patient. Preferred doses are from 1 mg to 10 mg/kg body weight, in addition to customary pharmaceutically innocuous excipients and additives.

The proposed therapeutics can be administered orally, e.g., in the form of pills, tablets, coated tablets, sugar coated tablets, hard and soft gelatin capsules, solutions, syrups, emulsions or suspensions. Administration, however, can also be carried out rectally, e.g., in the form of suppositories, or parenterally, e.g., in the form of injections or infusions or percutaneously, e.g., in the form of ointments, creams or tinctures.

In addition to the active compound of formula (I), the pharmaceutical composition can contain further customary, usually inert carrier materials or excipients, in particular as outlined above. Thus, the pharmaceutical preparations can also contain additives, such as, for fillers, extenders, disintegrants, binders, glidants, wetting agents, stabilizers, emulsifiers, preservatives, sweetening agents, colorants, flavorings or aromatizers, buffer substances, and furthermore solvents or solubilizers or agents for achieving a depot effect, as well as salts for changing the osmotic pressure, coating agents or antioxidants.

The compounds of the present disclosure can be used in the form of one substance alone or in combination with other active compounds—for example with remedies already known to improve reference memory of healthy individuals, in particular of healthy aging individuals.

The disclosure also provides a pharmaceutical composition comprising compounds of formula (I), in particular 5-((((S),(S)-3-bromophenyl)(phenyl)methyl)sulfinyl) methyl)thiazole, in free form or in the form of pharmaceutically acceptable formulations and together with pharmaceutically acceptable diluents or carriers.

The compounds of formula (I), in particular 5-((((S),(S)-3-halophenyl)(phenyl)methyl)sulfinyl)methyl)thiazole, more in particular 5-((((S),(S)-3-bromophenyl)(phenyl) methyl)sulfinyl)methyl)thiazole and even more in particular 5-((((S),(S)-3-bromophenyl)(phenyl)methyl)sulfinyl) methyl)-1,3-thiazole, and also the pharmaceutically acceptable salt or solvate thereof can be used as the active principle for improvement of as learning capabilities, in particular spatial learning capabilities, and memory performance, in particular reference memory, also in healthy or unimpaired individuals.

The compounds of the present disclosure according to Formula (I), in particular 5-((((S),(S)-3-halophenyl)(phenyl) methyl)sulfinyl)methyl)thiazole, more in particular 5-((((S),(S)-3-bromophenyl)(phenyl)methyl)sulfinyl) methyl)thiazole and even more in particular 5-((((S),(S)-3-bromophenyl)(phenyl)methyl)sulfinyl)methyl)-1,3-thiazole, are many times more effective and also many times more selective than for example Modafinil (2-(diphenylmethyl) sulfinyl acetamide).

The present disclosure also relates to the use of the compounds according to Formula (I), in particular 5-((((S),(S)-3-halophenyl)(phenyl)methyl)sulfinyl)methyl) thiazole, more in particular 5-((((S),(S)-3-bromophenyl) (phenyl)methyl)sulfinyl)methyl)thiazole and even more in particular 5-((((S),(S)-3-bromophenyl)(phenyl)methyl)sulfinyl)methyl)-1,3-thiazole, and also to the use of physiologically functional derivatives in the manufacture of a medicament for the improvement of learning capabilities, in particular spatial learning capabilities, and memory performance, in particular reference memory, of healthy individuals or aging individuals or of individuals with cognitive impairments, or for the treatment of a disease or a therapeutic indication in which improvement of learning capabilities and memory performance, and more in particular of spatial learning and memory tasks is beneficial.

Preferably, the pharmaceutical composition according to the present disclosure comprises the compound as defined by Formula (I), in particular 5-((((S),(S)-3-bromophenyl) (phenyl)methyl)sulfinyl)methyl)thiazole, in free form and a pharmaceutically acceptable diluent or carrier for use in the treatment of healthy individual or aging individuals or treatment of a disease or medical condition accompanied by deficits of learning capabilities and memory performance, and more in particular of spatial learning and memory tasks.

However, in general with the present disclosure also a pharmaceutical composition has been provided comprising the S enantiomer of the compound according to formula (I) and at least one pharmaceutically acceptable carrier and/or diluent, as defined herein, for use in therapy, i.e., for use as a medicament, in particular for treating age-related cognitive decline, more in particular for treating age-related cognitive decline according to 2018 ICD-10-CM Diagnosis Code R41.81, e.g., according to the US version of 2018 ICD-10-CM Diagnosis Code R41.81.

The compound according to Formula (I), in particular 5-((((S),(S)-3-bromophenyl)(phenyl)methyl)sulfinyl) methyl)thiazole, can in particular be used for improving learning capabilities, in particular spatial learning capabilities, and memory performance, in particular reference memory, with human individual who do not have defects of cognitive functions and/or reference memory deficits, or any such defects or deficits caused by diseases of the brain. Alternatively, the compound according to Formula (I), in particular 5-((((S),(S)-3-halophenyl)(phenyl)methyl)sulfinyl)methyl)thiazole, more in particular 5-((((S),(S)-3-bromophenyl)(phenyl)methyl)sulfinyl)methyl)thiazole and even more in particular 5-((((S),(S)-3-bromophenyl)(phenyl) methyl)sulfinyl)methyl)-1,3-thiazole, can be used for human individuals who have defects of cognitive functions and/or reference memory deficits caused by diseases of the brain. The causes for such defects of cognitive functions and/or reference memory deficits are those as mentioned above.

Accordingly, the problem of the present disclosure is also solved by the use of the compound according to Formula (I), in particular of 5-((((S),(S)-3-halophenyl)(phenyl)methyl)sulfinyl)methyl)thiazole, more in particular 5-((((S),(S)-3-bromophenyl)(phenyl)methyl)sulfinyl)methyl)thiazole and even more in particular 5-((((S),(S)-3-bromophenyl)(phenyl)methyl)sulfinyl)methyl)-1,3-thiazole, for the preparation of a medicament for improving the learning capabilities, in particular spatial learning capabilities, and memory performance, in particular reference memory, in human individuals, in particular in aging individuals. Preferably, said prepared medicament is used with human individual who do not have defects of cognitive functions and/or reference memory deficits, or any such defects or deficits caused by diseases of the brain. Alternatively, said medicament prepared by use of the e compound according to Formula (I), in particular 5-((((S),(S)-3-bromophenyl)(phenyl)methyl)sulfinyl)methyl)thiazole, can be used for treating human individuals who have defects of cognitive functions and/or reference memory deficits caused by diseases of the brain. The causes for such defects of cognitive functions and/or reference memory deficits are those as mentioned above.

It has also surprisingly been found that the compound according to Formula (I), in particular 5-((((S),(S)-3-halophenyl)(phenyl)methyl)sulfinyl)methyl)thiazole, more in particular 5-((((S),(S)-3-bromophenyl)(phenyl)methyl)sulfinyl)methyl)thiazole and even more in particular 5-((((S),(S)-3-bromophenyl)(phenyl)methyl)sulfinyl)methyl)-1,3-thiazole, can be used in improving the learning capabilities, in particular learning capabilities, and memory performance, in particular the reference memory, even in case of age-related memory decline. The surprising effects can for example be obtained by use of only 10 mg/kg and even only 1 mg/kg body weight for the compound according to Formula (I), in particular 5-((((S),(S)-3-halophenyl)(phenyl)methyl)sulfinyl)methyl)thiazole, more in particular 5-((((S),(S)-3-bromophenyl)(phenyl)methyl)sulfinyl)methyl)thiazole and even more in particular 5-((((S),(S)-3-bromophenyl)(phenyl)methyl)sulfinyl)methyl)-1,3-thiazole. It has also surprisingly been found that the compounds according to Formula (I), in particular 5-((((S),(S)-3-halophenyl)(phenyl)methyl)sulfinyl)methyl)thiazole, more in particular 5-((((S),(S)-3-bromophenyl)(phenyl)methyl)sulfinyl)methyl)thiazole and even more in particular 5-((((S),(S)-3-bromophenyl)(phenyl)methyl)sulfinyl)methyl)-1,3-thiazole, has a very high specificity and potential for DAT inhibition, and did not exhibit any unanticipated off-target activity. For example, with 5-((((S),(S)-3-bromophenyl)(phenyl)methyl)sulfinyl)methyl)thiazole) no agonist or antagonist activity against any of 157 G protein-coupled receptors (GPCRs) (from 66 GPCR families) tested in a functional cellular assay could be found. GPCRs are known to detect molecules outside the cell and activate internal signal transduction pathways that lead to cellular responses. The compounds of formula (I), in particular its (S),(S)-diastereomer, preferably in disastereomerically pure form, surprisingly exhibits a very low risk of or even essentially no risk of side effects. The final concentration of 0.22 μmol/l 5-((((S),(S)-3-bromophenyl)(phenyl)methyl)sulfinyl)-methyl)thiazole) in the profiler screen was achieved by serial dilution of a DMSO stock solution to the final assay concentration in 2.0% DMSO/Tris buffer. Cellular agonist effect was calculated as a % of control response to a known reference agonist for each target and cellular antagonist effect was calculated as a % inhibition of control reference agonist response for each target. Accordingly, the compounds according to Formula (I), in particular 5-((((S),(S)-3-halophenyl)(phenyl)methyl)sulfinyl)methyl)thiazole, more in particular 5-((((S),(S)-3-bromophenyl)(phenyl)methyl)sulfinyl)methyl)thiazole and even more in particular 5-((((S),(S)-3-bromophenyl)(phenyl)methyl)sulfinyl)methyl)-1,3-thiazole, appear to have an extremely low potential for off-target crossover.

It has also surprisingly been found that the compound according to Formula (I), in particular 5-((((S),(S)-3-halophenyl)(phenyl)methyl)sulfinyl)methyl)thiazole, more in particular 5-((((S),(S)-3-bromophenyl)(phenyl)methyl)sulfinyl)methyl)thiazole and even more in particular 5-((((S),(S)-3-bromophenyl)(phenyl)methyl)sulfinyl)methyl)-1,3-thiazole, can be used in the treatment and/or prevention of alcohol addiction, nicotine addiction or drug addiction, in particular in the treatment and/or prevention of cocaine and/or metamphetamine addiction, and even more in particular in the treatment and/or prevention of cocaine and metamphetamine addiction. Moreover, the present disclosure also provides a pharmaceutical preparation comprising the compound according to Formula (I), in particular 5-((((S),(S)-3-halophenyl)(phenyl)methyl)sulfinyl)methyl)thiazole, more in particular 5-((((S),(S)-3-bromophenyl)(phenyl)methyl)sulfinyl)methyl)thiazole and even more in particular 5-((((S),(S)-3-bromophenyl)(phenyl)methyl)sulfinyl)methyl)-1,3-thiazole for use in the treatment and/or prevention of alcohol addiction, nicotine addiction or drug addiction, in particular in the treatment and/or prevention of cocaine and/or metamphetamine addiction, and even more in particular in the treatment and/or prevention of cocaine and metamphetamine addiction.

And, it has also surprisingly been found that the compound according to Formula (I), in particular 5-((((S),(S)-3-halophenyl)(phenyl)methyl)sulfinyl)methyl)thiazole, more in particular 5-((((S),(S)-3-bromophenyl)(phenyl)methyl)sulfinyl)methyl)thiazole and even more in particular 5-((((S),(S)-3-bromophenyl)(phenyl)methyl)sulfinyl)methyl)-1,3-thiazole, are free or essentially free of any side effects such as increased states of arousal, depressive attacks or addiction problems.

Without being bound by any theory it is believed that the compounds of the present disclosure according to formula (I), and in particular 5-((((S),(S)-3-halophenyl)(phenyl)methyl)sulfinyl)methyl)thiazole, more in particular 5-((((S),(S)-3-bromophenyl)(phenyl)methyl)sulfinyl)methyl)thiazole and even more in particular 5-((((S),(S)-3-bromophenyl)(phenyl)methyl)sulfinyl)methyl)-1,3-thiazole, do not cause early after depolarizations (EADs) or changes in the duration and/or shape of the action potential by hERG (human Ether-a-go-go Related Gene). This action potential is specific for hERG. In this regard it is also believed that these compounds do not have any action on hERG.

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art and include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, /ert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Specifically preferred salt forms are hexaflorophosphate and chloride salts.

Such salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like. The term "physiologically acceptable cation" refers to a non-toxic, physiologically acceptable cationic counterion of an acidic functional group. Such cations are exemplified by sodium, potassium, calcium, magnesium, ammonium and tetraalkylammonium cations and the like.

The compounds according to the present disclosure may also be provided as solvates. "Solvate" refers to a compound provided herein or a salt thereof that further includes a stoichiometric or non-stoichiometric amount of solvent bound by non-covalent intermolecular forces. Where the solvent is water, the solvate is a hydrate.

EXAMPLES

Experimental Procedures Reaction conditions and yields were not systematically optimized. Anhydrous solvents were purchased from Sigma-Aldrich and were used as such without further purification. All other chemicals and reagents were purchased from VWR International, TCI Europe/Germany, Synthonix, Acros Organics, Activate Scientific, Fluorochem, Enamine and Alfa Aesar. 1H and 13C NMR spectra were recorded on a Bruker Avance 500 NMR spectrometer (UltraShield) using a 5-mm switchable probe (PA BBO 500SB BBF-H-D-05-Z, 1H, BB=19F and 31P-15N) with z axis gradients and automatic tuning and matching accessory (Bruker BioSpin). The resonance frequency for 1H NMR was 500.13 MHz and for 13C NMR 125.75 MHz. All measurements were performed for a solution in fully deuterated chloroform or DMSO at 298 K. Standard 1D and gradient-enhanced (ge) 2D experiments, like double quantum filtered (DQF) COSY, NOESY, HSQC, and HMBC, were used as supplied by the manufacturer. Chemical shifts are referenced internally to the residual, non-deuterated solvent signal for chloroform 1H (S=7.26 ppm) or DMSO 1H (δ=2.50 ppm) and to the carbon signal of the solvent for chloroform 13C (δ=77.00 ppm) or DMSO 13C (δ=39.57 ppm). HRESIMS spectra were obtained on a maXis HD ESI-Qq-TOF mass spectrometer (Bruker Daltonics, Bremen, Germany). Samples were dissolved to 20 μg/mL in MeOH and directly infused into the ESI source at a flow rate of 3 μL/min with a syringe pump. The ESI ion source was operated as follows: capillary voltage: 0.9 to 4.0 kV (individually optimized), nebulizer: 0.4 bar (N2), dry gas flow: 4 L/min (N2), and dry temperature: 200° C. Mass spectra were recorded in the range of m/z 50-1550 in the positive-ion mode. The sum formulas were determined using Bruker Compass DataAnalysis 4.2 based on the mass accuracy (Δm/z≤2 ppm) and isotopic pattern matching (SmartFormula algorithm). The purity of the compounds was determined by HPLC either on an UltiMate 3000 series system equipped with VWD detector (Dionex/Thermo Fisher Scientific, Germering, Germany) or on LC-2010A HT Liquid Chromatograph device (Shimadzu Corporation, Tokyo, Japan). Separation was carried out on an Acclaim 120 C18, 2.1×150 mm, 3 μm HPLC column (Thermo Fisher Scientific) using LC-MS-grade water and acetonitrile as mobile phase A and B, respectively. The sample components were separated and eluted with a linear gradient from 10% to 90% B in 25 min followed by an isocratic column cleaning and re-equilibration step. The flow rate was 0.2 mL/min and the column oven temperature was set to 25° C. The purity was determined from the UV chromatogram (254 nm) as the ratio of the peak area of the compound to the total peak area (i.e., the sum of the areas of all peaks that were not present in the solvent blank). Based on the HPLC data, all final compounds are ≥95% pure.

Syntheses of 5-((((3-bromophenyl)(phenyl)methyl) sulfinyl)methyl)thiazole diastereomers The synthesis of the diastereomers is depicted in FIG. 1. In the first step (a), 5-(chloromethyl)thiazole hydrochloride 1 and thioacetic acid 2 were reacted to yield S-(thiazol-5-ylmethyl) ethanethioate 3. In the following step (b), acylated intermediate was deprotected and the desired thiazol-5-ylmethanethiol 5 was isolated, that was further reacted with commercially available (3-bromophenyl)(phenyl)methanol 4 and $BF_3.Et_2O$ in $CH_3COOH$ in a condensation reaction (c) to provide a compound with sulfenyl moiety 6. The subsequent semi-preparative chiral HPLC separations (d) allowed isolation of individual enantiomers 7 and 8 with the configurations on the carbon atom 1 ($C_1$) being S and R, respectively. Oxidation of the sulfenyl intermediates 7 and 8 with $H_2O_2$ in $CH_3COOH$ (e), generated sulfoxide containing products noted as _mix_1 and _mix_2. Both products are the mixture of 2 stereoisomers. In the final step (f), semi-preparative chiral separations allowed isolation of individual stereoisomers, 1_1 and 1_2 from mix_1, as well as 2_1 and 2_2 from mix 2, respectively. All of the compounds have been unambiguously characterized (high-resolution mass spectrometry, high-resolution NMR-1D and 2D, HPLC-determined purity).

The reagents and conditions used for the individual reaction steps depicted in FIG. 1 can be summarized as follows: (a) $K_2CO_3$, NaI, acetone, 35-40° C., 3 h; (b) NaOH, EtOH, reflux, 2 h; (c) $BF_3.Et_2O$, $CH_3COOH$, room temperature overnight; (d) chiral separations, Chiralpack IA column, isocratic 100% EtOH as mobile phase; (e) $CH_3COOH$, $H_2O_2$, room temperature overnight; (f) chiral separations, Chiralpack IA column, (i) isocratic 100% EtOAC as mobile phase for 1_1 and 1_2, (ii) 100% EtOAC as mobile phase for 2_1 and 2_2. The purity the stereoisomeric compounds was determined by RP-HPLC method, and the enantiomeric excess (ee) of the stereoisomeric compounds was determined by chiral HPLC method.

Synthesis of Starting Materials

S-(thiazol-5-ylmethyl) ethanethioate (3)

A mixture of 5-(chloromethyl)-1,3-thiazole hydrochloride (1) (5.0 g, 29.4 mmol), thioacetic acid (2) (2.65 g, 32.11 mmol), potassium carbonate (10.5 g, 76 mmol) and acetone (100 ml) was stirred overnight at room temperature The precipitate was filtered off and washed with acetone. The filtrate and rinse were combined and evaporated in vacuum to minimal volume. Water (50 mL) and DCM (50 mL) were added to the residue and the mixture was stirred for 15 min. Layers were separated, the organic layer was washed with water, dried over $Na_2SO_4$ and the solvent was evaporated in vacuum. The resulting brownish oil was purified by flash-chromatography on silica gel (DCM) to give 3.78 g of 3 as yellowish oil (yield 74%).

Thiazol-5-ylmethanethiol was further condensed with (3-bromophenyl)(phenyl)methanol (4) to yield racemic 5-((((3-bromophenyl)(phenyl)methyl)thio)methyl)thiazole (6).

5-((((3-Bromophenyl)(phenyl)methyl)thio)methyl) thiazole (6)

1.0 g (6.6 mmol) of 3-bromobenzhydrol and (0.88 g, 6.6 mmol) of thiazol-5-ylmethanethiol were dissolved in glacial acetic acid. 1.1 equivalent (1.9 mL, 7.3 mmol) of $BF_3.Et_2O$ was added to a solution and reaction mixture was left under stirring overnight at room temperature. Reaction mixture was then poured over ice, a small amount of water was added and acetic acid was neutralized with addition of solid $NaHCO_3$. Product was then extracted (3×) with 50 ml of ethyl acetate. Organic layers were collected, combined, dried over anhydrous $Na_2SO_4$, filtered and concentrated under reduced pressure. Crude product was then purified by flash column chromatography on silica gel (petrolether/EtOAc=2/1) affording 0.48 g of 6 as the oily product (yield 19%)

In the following step, compound 6 was separated using CHIRALPACK IA semipreparative column (10 mm diameter×20 mm length) (Daicel Inc, Tokyo, Japan) and ethanol as the mobile phase into individual enantiomers 7 and 8. 40 mg/mL of 6 was applied per injection, flow rate of EtOH was set to 10 mL/min. Each of the enantiomers was further oxidized to yield again racemic compounds mix_1 and mix_2, respectively, that were finally separated using CHIRALPACK IA semipreparative column (25 mg/mL injection, EtOAc flow rate of 10 mL/min) into individual stereoisomers 1_1, 1_2, 2_1, 2_2. For all separations flow rate was set to 10 mL/min and all of the separations were carried out on the room temperature.

Attribution of Absolute Configuration (AC)

Attribution of absolute configuration (AC) of compounds 1_1, 1_2, 2_1, 2_2 was performed using vibrational-circular dichroism (VCD) method. Absolute configuration of diastereomer 1_1 was assigned as S1 (S) C1 (S), i.e., 1_1=5-((((S),(S)-3-bromophenyl)(phenyl)methyl)sulfinyl)methyl) thiazole; that of 1_2 was assigned S1 (R) C1 (S), i.e., 1_2=5-((((R),(S)-3-bromophenyl)(phenyl)methyl)sulfinyl) methyl)-thiazole; that of 2_1 was assigned S1 (S) C1 (R), i.e., 2_1=5-((((S),(R)-3-bromophenyl)(phenyl)methyl)sulfinyl)methyl)thiazole; and that of 2_2 was assigned S1 (R) C1 (R), i.e., 2_2=5-((((R),(R)-3-bromophenyl)(phenyl)methyl) sulfinyl)methyl)-thiazole.

Absolute configuration of diastereomer 1_1 was additionally confirmed by crystallographic data to be 5-((((S),(S)-3-bromophenyl)(phenyl)methyl)sulfinyl)methyl)thiazole.

Holeboard Test:

Animals and Keeping Conditions:

Three sets/cohorts of male Sprague-Dawley rats [18 months old n=10 per group; groups: vehicle-1 mg/kg bw-10 mg/kg bw of 1_1-treated, old behaviorally uncharacterized), 24 months old, poor memory aging group/inferior (n=10, groups vehicle, treated with 1 mg/kg bw of diastereomer 1_1) and 25 months old animals (n=10 per group; groups: all with intermediate level memory of aging rats, vehicle-1 mg/kg bw-10 mg/kg bw of diastereomer 1_1), bred and maintained in the Core Unit of Biomedical Research, Division of Laboratory Animal Science and Genetics, Medical University of Vienna were used. Animals were transferred to a separate experimental room one week before the start of the experimental procedure and kept there throughout the experiment individually in standard Makrolon cages filled with autoclaved woodchips temperature: 22±2° C.; humidity: 55±5%; 12 h artificial light/12 h dark cycle: light on at 7:00 am). The study was carried out according to the guidelines of the Ethics committee, Medical University of Vienna, and were approved by the Federal Ministry of Education, Science and Culture, Austria Holeboard Apparatus and Training:

The holeboard (1 m×1 m) was made from black plastic and surrounded by translucent plexiglass walls. The walls were equipped with spatial cues. Distal cues were provided by room structures outside the board. Four out of sixteen regularly arranged holes (diameter and depth 7 cm) were baited (dustless precision pellets, 45 mg, Bioserv®). The pattern of baited holes remained the same during the entire test. To avoid olfactory orientation pellets were also present in an area below the board. Prior to the experiment for three days the rats were handled for 15 min to get familiarized to the experimenter, followed by two days of habituation to the hole-board during which the animals could explore the maze for 15 min each day with access to food pellets. The weight of each rat was reduced by food restriction to reach 85% of its initial body weight before the start of the experiment. Tap water was given ad libitum. The rats were trained for three days (five trials on day one, four trials on day 2 and a retention trial at day 3). Every trial lasted for 120 s or until all four pellets were found. The apparatus was cleaned with 0.1% Incidin® (Ecolab, Dusseldorf, Germany) between trials to remove odor cues. The interval between two successive trials for an individual was 20 min. A camera mounted on the room ceiling recorded the performance of the rats in the maze. The hole visits and removals of pellets were noted for each trial. To compare rats with similar levels of motivation, rats with less than 40-hole visits in total over the ten trials were excluded from the analysis. Reference memory errors were noted as the number of visits to the unbaited holes. Reference Memory Index (RMI) was calculated using the formula (first+revisits of baited holes)/total visits of all holes. All behavioral training/testing was performed during the light phase of the light-dark cycle.

Figure 2:
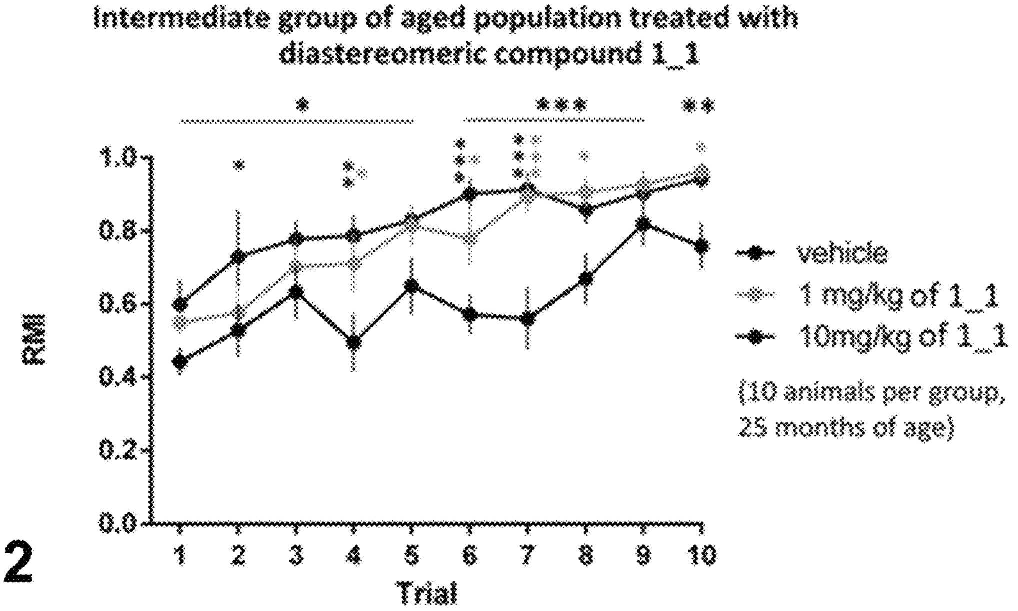
FIG. 2 shows the RMI for the intermediate group of aged population treated with diastereomeric compound 1_1.

Results on Learning and Memory in the Holeboard:

FIG. 2 shows the RMI for the intermediate group of aged population treated with diastereomeric compound 1_1 at 1 mg/kg dose and 10 mg/kg dose.

Figure 3:
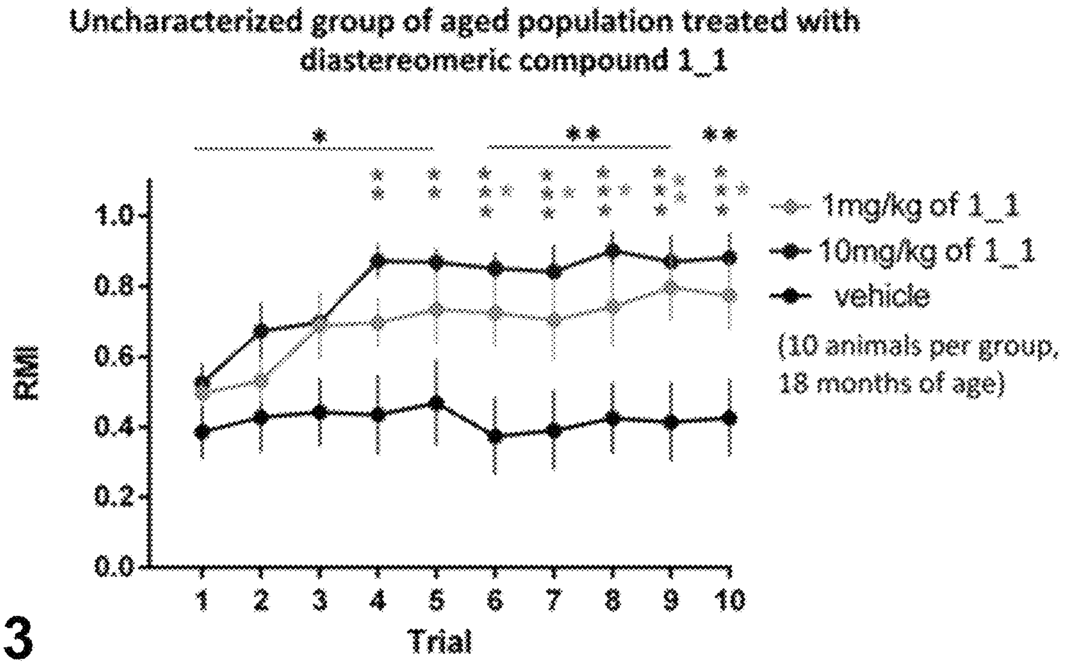
FIG. 3 shows the RMI for the uncharacterized group of aged population treated with diastereomeric compound 1_1.

FIG. 3 shows the RMI for the uncharacterized group of aged population treated with diastereomeric compound 1_1 at 1 mg/kg dose and 10 mg/kg dose.

Figure 4:
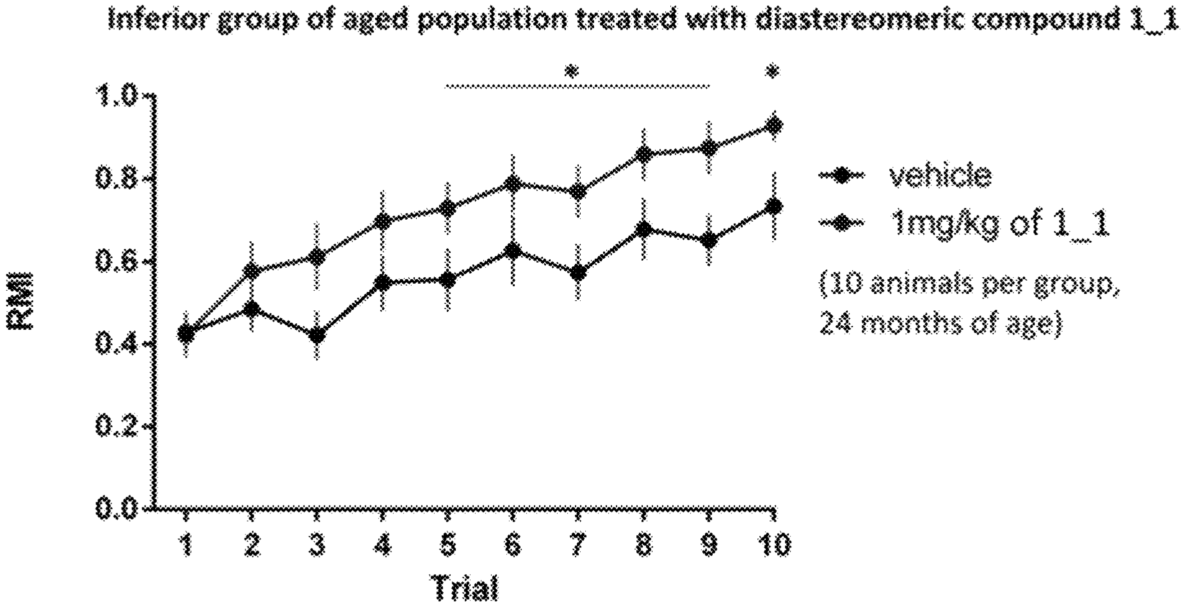
FIG. 4 shows the RMI for the inferior group of aged population treated with diastereomeric compound 1_1.

FIG. 4 shows the RMI for the inferior group of aged population treated with diastereomeric compound 1_1 at 1 mg/kg dose and 10 mg/kg dose.

Monoamine Transporter Reuptake Inhibition

Uptake inhibition measurements were performed as described in S. Sucic et al. (The N Terminus of Monoamine Transporters Is a Lever Required for the Action of Amphetamines. J. Biol. Chem. 2010, 285 (14), 10924-10938) and Kalaba et al. (Heterocyclic Analogues of Modafinil as Novel, Atypical Dopamine Transporter Inhibitors. J. Med.

Chem. 2017, 60 (22), 9330-9348). Dulbecco's modified Eagle's medium (DMEM), trypsin and fetal calf serum (FCS) were purchased from Sigma-Aldrich Handels GmbH (Austria). [3H]5-HT (Hydroxytryptamine creatinine sulfate; 5-[1,2-3H[N]]; 45.3 Ci/mmol), [3H]DA (Dihydroxyphenylethylamine; 3,4-[ring-2,5,6-3[H]]-Dopamine; 55.8 Ci/mmol) and [3H]MPP+(Methyl-4-phenylpyridinium iodide; 1-[methyl-3H]; 80 Ci/mmol) were purchased from Perkin Elmer, Boston, MA. Inhibition of the DAT, NET, and SERT was assessed in human embryonic kidney 293 (HEK 293) that stably express the human DAT, NET, and SERT. Cells were grown as monolayers in 96-well plates precoated with poly-D-lysine (PDL) (4×104 cells/well) 24 h prior to the experiment. On the day of the experiment, the medium was aspirated, and each well was washed with warm (30° C.) 0.1 mL of Krebs-HEPES buffer (KHB; 10 mM HEPES, 120 mM NaCl, 3 mM KCl, 2 mM $CaCl_2.2H_2O$, 2 mM $MgCl_2.6H_2O$, 5 mM D-(+)-Glucose monohydrate, pH 7.3). The cells were pre-incubated for 5 min in KHB containing 1% of dimethyl sulfoxide and increasing concentrations of the test compound. After aspiration of the preincubation solution, the cells were incubated in KHB containing increasing concentrations of the compound with the addition of 0.2 μM [3H]-dopamine (for DAT), 0.02 μM [3H]-MPP+ (for NET) and 0.2 μM [3H]-5-HT (for SERT). Incubation times were 1 min for DAT and SERT and 3 min for NET. Non-specific [3H]-dopamine and [3H]-MPP+ uptake in the presence of 30 μM cocaine was subtracted from total uptake. Non-specific [3H]-5-HT uptake in the presence of 30 μM paroxetine was subtracted from total uptake. After incubation at room temperature, reactions were stopped by the addition of 0.1 mL of ice-cold KHB. Finally, cells were lysed with 0.3 mL of 1% SDS and released radioactivity was measured by a liquid scintillation counter (Tri-carb-2300TR, Perkin Elmer). Non-linear regression analysis (GraphPad Prism version 5.0, GraphPad Software, San Diego, CA, USA) was used for calculation of $IC_{50}$ values.

TABLE[1)]

| Compound | DAT $IC_{50}$ (μM) ± SD | NET | SERT |
|---|---|---|---|
| (R)[2)] | 0.85 ± 0.13 | 17.2 ± 4.5 | NS |
| (1_1) | 0.22 ± 0.06 | 11.7 ± 7.3 | NS |
| (1_2) | 5.6 ± 1.0 | 148.1 ± 68.4 | NS |
| (2_1) | 2.7 ± 1.4 | NS | NS |
| (2_2) | 1.2 ± 0.4 | 13.9 ± 15.9 | NS |

[1)]Values are means of at least three independent experiments.
NS—Not specific in the used concentration range;
[2)]Diastereomeric mixture of (1_1, 1_2, 2_1 and 2_2).

As could be shown, the compounds of the present disclosure effectively and selectively inhibit the dopamine transporter (DAT) thereby inhibiting reuptake of extracellular dopamine into the synapse and increasing the extracellular concentration of dopamine, which then leads to improved learning capabilities, in particular spatial learning capabilities, and/or to an improved reference memory. Different from commonly used inhibitors, DAT inhibition is rather specific, and noradrenaline and serotonin transporters are not or at least not remarkably inhibited with the compounds of the present disclosure, in particular not with 5-((((S),(S)-3-halophenyl)(phenyl)methyl)sulfinyl)methyl) thiazole, more in particular not or at least not remarkably inhibited with 5-((((S),(S)-3-bromophenyl)(phenyl)methyl) sulfinyl)methyl)thiazole and even more in particular not or at least not remarkably inhibited with 5-((((S),(S)-3-bromophenyl)(phenyl)methyl)sulfinyl)methyl)-1,3-thiazole. Consequently, with the use of the compounds of the present disclosure unwanted side effects may be omitted.

Although modifications and changes maybe suggested by those skilled in the art, it is the intention of the applicant to embody within the patent warranted hereon all changes and modifications as reasonably and probably come within the scope of this contribution to the art. The features of the present disclosure which are believed to be novel are set forth in detail in the appended claims. The features disclosed in the description, the figures as well as the claims could be essential alone or in every combination for the realization of the disclosure in its different embodiments.

The invention claimed is:

1. A chemical compound being 5-((((S), (S)-3-bromophenyl)(phenyl)methyl)sulfinyl)methyl)thiazole.

2. The chemical compound according to claim 1 being 5-((((S),(S)-3-bromophenyl)(phenyl)methyl)sulfinyl) methyl)-1,3-thiazole.

3. A method for treating age-related cognitive decline in a human individual, wherein the method comprises administering to the human individual a therapeutically effective amount of the compound of claim 1.

4. The method according to claim 3, wherein
the human individual does not have defects of cognitive functions and/or reference memory deficits and/or motivation deficits.

5. The method according to claim 3, wherein
the human individual has defects of cognitive functions, and/or reference memory deficits, and/or motivation deficits caused by diseases of the brain.

6. The method according to claim 5, wherein
the human individual has defects of cognitive functions and/or reference memory deficits and/or motivation deficits, reference memory deficits or defects of cognitive functions or reference memory deficits and defects of cognitive functions, caused by Alzheimer; Down syndrome; vascular cognitive impairment; stroke; frontotemporal dementia; behavioural, semantic or progressive aphasia type dementia; dementia with Lewy bodies; subcortical dementias; Parkinson's disease dementia; alcohol related dementia; dementia caused by traumatic brain injury; Huntington's disease related dementia; AIDS-related dementia; attention deficit disorders; reference memory deficiencies related to ageing; reference memory disorders related to viral infections of the brain; endogenous psychotic disorders.

7. The method according to claim 6, wherein
the defects of cognitive functions and/or reference memory deficits and/or motivation deficits are caused by schizophrenia.

8. A method for inhibiting DAT-mediated dopamine reuptake in the synapses in the brain of a human individual, wherein the method comprises administering to the human individual a therapeutically effective amount of the compound of claim 1.

9. A method for improving cognitive functions in a human individual, wherein the method comprises administering to the human individual a therapeutically effective amount of the compound of claim 1.

10. The method according to claim 9, wherein
the cognitive functions to be improved include learning capability, and/or memory performance in human individuals.

11. The method according to claim 9, wherein the human individuals do not have defects of cognitive functions and/or reference memory deficits and/or motivation deficits.

12. A pharmaceutical preparation comprising at least one compound according to claim 1 and a pharmaceutically acceptable carrier and/or diluent.

13. A method for treating alcohol addiction, nicotine addiction or drug addiction, wherein the method comprises administering to the human individual a therapeutically effective amount of the compound of claim 1.

* * * * *